US010073095B2

(12) United States Patent
Mehra et al.

(10) Patent No.: US 10,073,095 B2
(45) **Date of Patent: *Sep. 11, 2018**

(54) PEPTIDES AND METHODS FOR THE DETECTION OF LYME DISEASE ANTIBODIES

(71) Applicant: ABAXIS, INC., Union City, CA (US)

(72) Inventors: Rajesh K. Mehra, Hayward, CA (US); Kenneth P. Aron, San Francisco, CA (US); Dennis M. Bleile, San Ramon, CA (US); Jeremy Walker, Castro Valley, CA (US); Cristina Cuesico, Fremont, CA (US)

(73) Assignee: Abaxis, Inc., Union City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/684,635

(22) Filed: Aug. 23, 2017

(65) Prior Publication Data

US 2017/0356910 A1 Dec. 14, 2017

Related U.S. Application Data

(60) Division of application No. 14/924,358, filed on Oct. 27, 2015, now Pat. No. 9,766,238, which is a (Continued)

(51) Int. Cl.
*A61K 39/00* (2006.01)
*A61K 39/02* (2006.01)
(Continued)

(52) U.S. Cl.
CPC ........ *G01N 33/56911* (2013.01); *C07K 14/20* (2013.01); *G01N 2333/20* (2013.01); *G01N 2469/20* (2013.01)

(58) Field of Classification Search
CPC ........ A61K 39/00; A61K 39/02; A61K 39/38; C07K 14/20; G01N 33/569
(Continued)

(56) References Cited

U.S. PATENT DOCUMENTS

| | | | |
|---|---|---|---|
| 4,721,617 | A | 1/1988 | Johnson |
| 4,888,276 | A | 12/1989 | Shelburne |

(Continued)

FOREIGN PATENT DOCUMENTS

| | | | |
|---|---|---|---|
| WO | WO 2000/065064 A1 | 11/2000 | |
| WO | WO 2002/090961 A2 | 11/2002 | |

(Continued)

OTHER PUBLICATIONS

Eicken et al., "Crystal Structure of Lyme Disease Variable Surface Antigen VlsE of Borrelia burgdorferi," J. Biol. Chem., vol. 277: 21691-21696, 2002.

(Continued)

*Primary Examiner* — Jana A Hines
(74) *Attorney, Agent, or Firm* — Cooley LLP

(57) ABSTRACT

The invention provides compositions (e.g., peptide compositions) useful for the detection of antibodies that bind to *Borrelia* antigens. The peptide compositions comprise polypeptide sequences comprising variants in the IR6 domain of the *Borrelia* VlsE protein. The invention also provides devices, methods, and kits comprising such peptide compositions and useful for the detection of antibodies that bind to *Borrelia* antigens and the diagnosis of Lyme disease.

12 Claims, 5 Drawing Sheets

Specification includes a Sequence Listing.

Related U.S. Application Data continuation of application No. 14/304,809, filed on Jun. 13, 2014, now Pat. No. 9,201,071, which is a continuation of application No. 13/667,909, filed on Nov. 2, 2012, now Pat. No. 8,758,772.

(60) Provisional application No. 61/556,061, filed on Nov. 4, 2011.

(51) Int. Cl.
*A61K 39/38* (2006.01)
*G01N 33/569* (2006.01)
*C07K 14/20* (2006.01)

(58) Field of Classification Search
USPC ......... 424/184.1, 185.1, 190.1, 203.1, 234.1, 424/278.1; 435/4, 6, 6.15, 7.1, 7.2, 7.32, 435/7.92; 436/536, 538
See application file for complete search history.

(56) References Cited

U.S. PATENT DOCUMENTS

| | | | |
|---|---|---|---|
| 5,155,022 | A | 10/1992 | Naqui et al. |
| 5,178,859 | A | 1/1993 | Simon et al. |
| 5,187,065 | A | 2/1993 | Schutzer |
| 5,308,753 | A | 5/1994 | Dorward et al. |
| 5,324,630 | A | 6/1994 | LeFebvre et al. |
| 5,385,826 | A | 1/1995 | Schell et al. |
| 5,494,797 | A | 2/1996 | McCann et al. |
| 5,618,533 | A | 4/1997 | Flavell et al. |
| 5,620,862 | A | 4/1997 | Padula |
| 5,747,294 | A | 5/1998 | Flavell et al. |
| 5,977,339 | A | 11/1999 | LeFebvre et al. |
| 6,221,363 | B1 | 4/2001 | Livey et al. |
| 6,437,116 | B1 | 8/2002 | Norris et al. |
| 6,475,492 | B1 | 11/2002 | Philipp et al. |
| 6,613,331 | B1 | 9/2003 | Simon et al. |
| 6,660,274 | B2 | 12/2003 | Philipp |
| 6,665,652 | B1 | 12/2003 | Porwancher |
| 6,667,038 | B1 | 12/2003 | Donta et al. |
| 6,716,574 | B2 | 4/2004 | Mathiesen et al. |
| 6,719,983 | B2 | 4/2004 | Norris et al. |
| 6,740,744 | B2 | 5/2004 | Norris et al. |
| 6,838,247 | B2 | 1/2005 | Whitaker et al. |
| 6,902,893 | B1 | 6/2005 | Choi et al. |
| 7,135,176 | B2 | 11/2006 | Norris et al. |
| 7,847,084 | B2 | 12/2010 | Norris |
| 8,071,109 | B2 | 12/2011 | Norris et al. |
| 8,076,470 | B2 | 12/2011 | Norris |
| 8,211,711 | B2 | 7/2012 | Nazareth et al. |
| 8,232,045 | B2 | 7/2012 | Charlton |
| 8,283,458 | B2 | 10/2012 | Norris |
| 8,568,989 | B2 | 10/2013 | Mehra et al. |
| 8,758,772 | B2 | 6/2014 | Mehra et al. |
| 9,201,071 | B2 | 12/2015 | Mehra et al. |
| 9,766,238 | B2 | 9/2017 | Mehra et al. |
| 2003/0129680 | A1 | 7/2003 | O'Connor |
| 2006/0194267 | A1 | 8/2006 | Vojdani |
| 2006/0240035 | A1 | 10/2006 | Norris |
| 2009/0246861 | A1 | 10/2009 | Manabe |
| 2010/0330585 | A1 | 12/2010 | Kabri |
| 2011/0008910 | A1 | 1/2011 | Van Boekel et al. |
| 2011/0136155 | A1 | 6/2011 | Mehra et al. |
| 2013/0115634 | A1 | 5/2013 | Mehra et al. |
| 2014/0364332 | A1 | 12/2014 | Mehra et al. |
| 2016/0109446 | A1 | 4/2016 | Mehra et al. |

FOREIGN PATENT DOCUMENTS

| | | | |
|---|---|---|---|
| WO | WO 2007/133623 | A2 | 11/2007 |
| WO | WO 2011/063003 | A2 | 5/2011 |
| WO | WO 2013/067524 | A1 | 5/2013 |

OTHER PUBLICATIONS

Embers et al., "Dominant Epitopes of the C6 Diagnostic Peptide of Borrelia burgdorferi are Largely Inaccessible to Antibody on the Parent VIsE Molecule," Clin. Vaccine Immunol., vol. 14(8): 931-936, 2007.
European Search Report for Application No. EP 12846033.4 dated Apr. 1, 2015, 2 pages.
Gomes-Solecki et al., "Epitope Length, Genospecies Dependency, and Serum Panel Effect in the IR6 Enzyme-Linked Immunosorbent Assay for Detection of Antibodies to Borrelia burgdorferi," Clin. Vaccine Immunol., vol. 14(7): 875-879, 2007.
Hamby et al., "Use of Peptide Library Screening to Detect a Previously Unknown Linear Diagnostic Epitope: Proof of Principle by Use of Lyme Disease Sera," Clin. Diagn. Lab Immunol., vol. 12(7): 801-807, 2005.
International Preliminary Report on Patentability for International Application No. PCT/US2010/057053 dated May 22, 2012, 5 pages.
International Preliminary Report on Patentability, 10 pages, International Patent Appl. No. PCT/U52012/063594, dated May 6, 2014.
International Search Report and Written Opinion, 10 pages, International Patent Appl. No. PCT/US2012/063594, U.S. Patent and Trademark Office, dated Feb. 15, 2013.
International Search Report, 6 pages, International Patent Appl. No. PCT/US2010/057053, Korean Intellectual Property Office (dated Jul. 13, 2011).
Jobe et al., "Significantly Improved Accuracy of Diagnosis of Early Lyme Disease by Peptide Enzyme-Linked Immunosorbent Assay Based on the Borreliacidal Antibody Epitope of Borrelia burgdorferi OspC," Clin. Vaccine Immunol., vol. 15(6): 981-985, 2008.
Lafleur et al., "Bacterin That Induces Anti-OspA and Anti-OspC Borreliacidal Antibodies Provides a High Level of Protection against Canine Lyme Disease," Clin. Vaccine Immunol., vol. 16(2): 253-259, 2009.
Ledue et al., "Evaluation of the Recombinant VIsE-Based Liaison Chemiluminescence Immunoassay for Detection of Borrelia burgdorferi and Diagnosis of Lyme Disease," Clin. Vaccine Immunol., vol. 15(12): 1796-1804, 2008.
Liang et al., "Characterization of a Borrelia burgdorferi VIsE Invariable Region Useful in Canine Lyme Disease Serodiagnosis by Enzyme-Linked Immunosorbent Assay," J. Clin. Microbiol., vol. 38(11):4160-4166, 2000.
Liang et al., "Sensitive and Specific Serodiagnosis of Lyme Disease by Enzyme-Linked Immunosorbent Assay with a Peptide Based o n. An Immunodominant Conserved Region of Borrelia burgdorferi VIsE," J. Clin. Microbiol. vol. 37(12): 3990-3996, 1999.
Marques, A.R., et al., "Evaluation of the C6 Peptide Enzyme-Linked Immunosorbent Assay for Individuals Vaccinated with the Recombinant OspA Vaccine." J. Olin. Microbial. (2002); 40(7): 2591-2593.
Non-Final Office Action for U.S. Appl. No. 12/948,209, dated Jan. 14, 2013.
Notice of Allowance for U.S. Appl. No. 12/948,209, dated Jun. 19, 2013.
O'Connor et al., "Dogs Vaccinated with Common Lyme Disease Vaccines Do Not Respond to IR6 , the Conserved Immunodominant Region of the VIsE Surface Protein of Borrelia burgdorferi," Clin. Diag. Lab. Immunol., vol. 11(3):458-462, 2004.
Sillanpaa et al., "Immune responses to borrelial VIsE IR6 peptide variants," Int. J. Med. Microbiol., vol. 297:45-52, 2007.
Supplementary European Search Report for European Application No. 10832113.4 dated Jun. 28, 2013.
Tjernberg et al., "Antibody responses to borrelia IR6 peptide variants and the C6 peptide in Swedish patients with erythema migrans," International Journal of Medical Microbiology, vol. 299: 439-446, 2009.
Wagner et al., "A fluorescent bead-based multiplex assay for the simultaneous detection of antibodies to B. burgdorferi outer surface proteins in canine serum," Vet. Immunol. Immunopathol., vol. 140: 190-198, 2011.

(56) References Cited

OTHER PUBLICATIONS

Written Opinion of the International Searching Authority, 4 pages, International Patent Appl. No. PCT/US2010/057053, Korean Intellectual Property Office, dated Jul. 13, 2011.

SEQUENCE LISTING

```
<160> NUMBER OF SEQ ID NOS: 152

<210> SEQ ID NO 1
<211> LENGTH: 25
<212> TYPE: PRT
<213> ORGANISM: Borrelia sp.
<220> FEATURE:
<221> NAME/KEY: MISC_FEATURE
<222> LOCATION: (11)..(11)
<223> OTHER INFORMATION: Xaa may be Val or Leu
<220> FEATURE:
<221> NAME/KEY: MISC_FEATURE
<222> LOCATION: (16)..(16)
<223> OTHER INFORMATION: Xaa may be Leu or Ile
<220> FEATURE:
<221> NAME/KEY: MISC_FEATURE
<222> LOCATION: (17)..(17)
<223> OTHER INFORMATION: Xaa may be Ala or Val
<220> FEATURE:
<221> NAME/KEY: MISC_FEATURE
<222> LOCATION: (21)..(21)
<223> OTHER INFORMATION: Xaa may be Arg, Asp or Asn
<220> FEATURE:
<221> NAME/KEY: MISC_FEATURE
<222> LOCATION: (24)..(24)
<223> OTHER INFORMATION: Xaa may be Ile, Trp or Tyr
<220> FEATURE:
<221> NAME/KEY: MISC_FEATURE
<222> LOCATION: (25)..(25)
<223> OTHER INFORMATION: Xaa may be Lys or Arg

<400> SEQUENCE: 1

Leu Lys Lys Asp Asp Asn Ile Ala Ala Ala Xaa Val Leu Arg Gly Xaa
1               5                   10                  15

Xaa Lys Asp Gly Xaa Phe Ala Xaa Xaa
            20                  25


<210> SEQ ID NO 2
<211> LENGTH: 48
<212> TYPE: PRT
<213> ORGANISM: Borrelia sp.
<220> FEATURE:
<221> NAME/KEY: MISC_FEATURE
<222> LOCATION: (1)..(1)
<223> OTHER INFORMATION: Xaa may be Ala or Val
<220> FEATURE:
<221> NAME/KEY: MISC_FEATURE
<222> LOCATION: (2)..(2)
<223> OTHER INFORMATION: Xaa may be Glu or Asp
<220> FEATURE:
<221> NAME/KEY: MISC_FEATURE
<222> LOCATION: (5)..(5)
<223> OTHER INFORMATION: Xaa may be Lys or Arg
```

```
<220> FEATURE:
<221> NAME/KEY: MISC_FEATURE
<222> LOCATION: (6)..(6)
<223> OTHER INFORMATION: Xaa may be Lys or Arg
<220> FEATURE:
<221> NAME/KEY: MISC_FEATURE
<222> LOCATION: (18)..(18)
<223> OTHER INFORMATION: Xaa may be Val or Leu
<220> FEATURE:
<221> NAME/KEY: MISC_FEATURE
<222> LOCATION: (23)..(23)
<223> OTHER INFORMATION: Xaa may be Leu or Ile
<220> FEATURE:
<221> NAME/KEY: MISC_FEATURE
<222> LOCATION: (24)..(24)
<223> OTHER INFORMATION: Xaa may be Ala or Val
<220> FEATURE:
<221> NAME/KEY: MISC_FEATURE
<222> LOCATION: (28)..(28)
<223> OTHER INFORMATION: Xaa may be Arg, Asp or Asn
<220> FEATURE:
<221> NAME/KEY: MISC_FEATURE
<222> LOCATION: (31)..(31)
<223> OTHER INFORMATION: Xaa may be Ile, Trp or Tyr
<220> FEATURE:
<221> NAME/KEY: MISC_FEATURE
<222> LOCATION: (32)..(32)
<223> OTHER INFORMATION: Xaa may be Lys or Arg
<220> FEATURE:
<221> NAME/KEY: MISC_FEATURE
<222> LOCATION: (35)..(35)
<223> OTHER INFORMATION: Xaa may be Gln or Arg
<220> FEATURE:
<221> NAME/KEY: MISC_FEATURE
<222> LOCATION: (38)..(38)
<223> OTHER INFORMATION: Xaa may be Val or Ala

<400> SEQUENCE: 2

Xaa Xaa Ser Pro Xaa Xaa Pro Leu Lys Lys Asp Asp Asn Ile Ala Ala
1               5                   10                  15

Ala Xaa Val Leu Arg Gly Xaa Xaa Lys Asp Gly Xaa Phe Ala Xaa Xaa
            20                  25                  30

Ala Val Xaa Glu Gly Xaa Gln Gln Glu Gly Ala Gln Gln Pro Ser Cys
        35                  40                  45


<210> SEQ ID NO 3
<211> LENGTH: 25
<212> TYPE: PRT
<213> ORGANISM: Borrelia sp.

<400> SEQUENCE: 3

Leu Lys Lys Asp Asp Asn Ile Ala Ala Ala Val Val Leu Arg Gly Leu
1               5                   10                  15

Ala Lys Asp Gly Arg Phe Ala Ile Lys
            20                  25


<210> SEQ ID NO 4
<211> LENGTH: 25
<212> TYPE: PRT
<213> ORGANISM: Borrelia sp.

<400> SEQUENCE: 4

Leu Lys Lys Asp Asp Asn Ile Ala Ala Ala Leu Val Leu Arg Gly Leu
1               5                   10                  15

Ala Lys Asp Gly Arg Phe Ala Ile Lys
            20                  25


<210> SEQ ID NO 5
<211> LENGTH: 25
```

-continued

<212> TYPE: PRT
<213> ORGANISM: Borrelia sp.

<400> SEQUENCE: 5

Leu Lys Lys Asp Asp Asn Ile Ala Ala Ala Val Val Leu Arg Gly Ile
1 5 10 15

Ala Lys Asp Gly Arg Phe Ala Ile Lys
20 25

<210> SEQ ID NO 6
<211> LENGTH: 25
<212> TYPE: PRT
<213> ORGANISM: Borrelia sp.

<400> SEQUENCE: 6

Leu Lys Lys Asp Asp Asn Ile Ala Ala Ala Leu Val Leu Arg Gly Ile
1 5 10 15

Ala Lys Asp Gly Arg Phe Ala Ile Lys
20 25

<210> SEQ ID NO 7
<211> LENGTH: 25
<212> TYPE: PRT
<213> ORGANISM: Borrelia sp.

<400> SEQUENCE: 7

Leu Lys Lys Asp Asp Asn Ile Ala Ala Ala Val Val Leu Arg Gly Leu
1 5 10 15

Val Lys Asp Gly Arg Phe Ala Ile Lys
20 25

<210> SEQ ID NO 8
<211> LENGTH: 25
<212> TYPE: PRT
<213> ORGANISM: Borrelia sp.

<400> SEQUENCE: 8

Leu Lys Lys Asp Asp Asn Ile Ala Ala Ala Leu Val Leu Arg Gly Leu
1 5 10 15

Val Lys Asp Gly Arg Phe Ala Ile Lys
20 25

<210> SEQ ID NO 9
<211> LENGTH: 25
<212> TYPE: PRT
<213> ORGANISM: Borrelia sp.

<400> SEQUENCE: 9

Leu Lys Lys Asp Asp Asn Ile Ala Ala Ala Val Val Leu Arg Gly Ile
1 5 10 15

Val Lys Asp Gly Arg Phe Ala Ile Lys
20 25

<210> SEQ ID NO 10
<211> LENGTH: 25
<212> TYPE: PRT
<213> ORGANISM: Borrelia sp.

<400> SEQUENCE: 10

Leu Lys Lys Asp Asp Asn Ile Ala Ala Ala Leu Val Leu Arg Gly Ile
1 5 10 15

Val Lys Asp Gly Arg Phe Ala Ile Lys
20 25

<210> SEQ ID NO 11
<211> LENGTH: 25
<212> TYPE: PRT
<213> ORGANISM: Borrelia sp.

<400> SEQUENCE: 11

Leu Lys Lys Asp Asp Asn Ile Ala Ala Ala Val Val Leu Arg Gly Leu
1 5 10 15

Ala Lys Asp Gly Asp Phe Ala Ile Lys
20 25

<210> SEQ ID NO 12
<211> LENGTH: 25
<212> TYPE: PRT
<213> ORGANISM: Borrelia sp.

<400> SEQUENCE: 12

Leu Lys Lys Asp Asp Asn Ile Ala Ala Ala Leu Val Leu Arg Gly Leu
1 5 10 15

Ala Lys Asp Gly Asp Phe Ala Ile Lys
20 25

<210> SEQ ID NO 13
<211> LENGTH: 25
<212> TYPE: PRT
<213> ORGANISM: Borrelia sp.

<400> SEQUENCE: 13

Leu Lys Lys Asp Asp Asn Ile Ala Ala Ala Val Val Leu Arg Gly Ile
1 5 10 15

Ala Lys Asp Gly Asp Phe Ala Ile Lys
20 25

<210> SEQ ID NO 14
<211> LENGTH: 25
<212> TYPE: PRT
<213> ORGANISM: Borrelia sp.

<400> SEQUENCE: 14

Leu Lys Lys Asp Asp Asn Ile Ala Ala Ala Leu Val Leu Arg Gly Ile
1 5 10 15

Ala Lys Asp Gly Asp Phe Ala Ile Lys
20 25

<210> SEQ ID NO 15
<211> LENGTH: 25
<212> TYPE: PRT
<213> ORGANISM: Borrelia sp.

<400> SEQUENCE: 15

Leu Lys Lys Asp Asp Asn Ile Ala Ala Ala Val Val Leu Arg Gly Leu
1 5 10 15

Val Lys Asp Gly Asp Phe Ala Ile Lys
20 25

<210> SEQ ID NO 16
<211> LENGTH: 25
<212> TYPE: PRT
<213> ORGANISM: Borrelia sp.

-continued

<400> SEQUENCE: 16

Leu Lys Lys Asp Asp Asn Ile Ala Ala Ala Leu Val Leu Arg Gly Leu
1 5 10 15

Val Lys Asp Gly Asp Phe Ala Ile Lys
20 25

<210> SEQ ID NO 17
<211> LENGTH: 25
<212> TYPE: PRT
<213> ORGANISM: Borrelia sp.

<400> SEQUENCE: 17

Leu Lys Lys Asp Asp Asn Ile Ala Ala Ala Val Val Leu Arg Gly Ile
1 5 10 15

Val Lys Asp Gly Asp Phe Ala Ile Lys
20 25

<210> SEQ ID NO 18
<211> LENGTH: 25
<212> TYPE: PRT
<213> ORGANISM: Borrelia sp.

<400> SEQUENCE: 18

Leu Lys Lys Asp Asp Asn Ile Ala Ala Ala Leu Val Leu Arg Gly Ile
1 5 10 15

Val Lys Asp Gly Asp Phe Ala Ile Lys
20 25

<210> SEQ ID NO 19
<211> LENGTH: 25
<212> TYPE: PRT
<213> ORGANISM: Borrelia sp.

<400> SEQUENCE: 19

Leu Lys Lys Asp Asp Asn Ile Ala Ala Ala Val Val Leu Arg Gly Leu
1 5 10 15

Ala Lys Asp Gly Asn Phe Ala Ile Lys
20 25

<210> SEQ ID NO 20
<211> LENGTH: 25
<212> TYPE: PRT
<213> ORGANISM: Borrelia sp.

<400> SEQUENCE: 20

Leu Lys Lys Asp Asp Asn Ile Ala Ala Ala Leu Val Leu Arg Gly Leu
1 5 10 15

Ala Lys Asp Gly Asn Phe Ala Ile Lys
20 25

<210> SEQ ID NO 21
<211> LENGTH: 25
<212> TYPE: PRT
<213> ORGANISM: Borrelia sp.

<400> SEQUENCE: 21

Leu Lys Lys Asp Asp Asn Ile Ala Ala Ala Val Val Leu Arg Gly Ile
1 5 10 15

Ala Lys Asp Gly Asn Phe Ala Ile Lys
20 25

<210> SEQ ID NO 22
<211> LENGTH: 25
<212> TYPE: PRT
<213> ORGANISM: Borrelia sp.

<400> SEQUENCE: 22

```
Leu Lys Lys Asp Asp Asn Ile Ala Ala Ala Leu Val Leu Arg Gly Ile
1               5                   10                  15

Ala Lys Asp Gly Asn Phe Ala Ile Lys
            20                  25
```

<210> SEQ ID NO 23
<211> LENGTH: 25
<212> TYPE: PRT
<213> ORGANISM: Borrelia sp.

<400> SEQUENCE: 23

```
Leu Lys Lys Asp Asp Asn Ile Ala Ala Ala Val Val Leu Arg Gly Leu
1               5                   10                  15

Val Lys Asp Gly Asn Phe Ala Ile Lys
            20                  25
```

<210> SEQ ID NO 24
<211> LENGTH: 25
<212> TYPE: PRT
<213> ORGANISM: Borrelia sp.

<400> SEQUENCE: 24

```
Leu Lys Lys Asp Asp Asn Ile Ala Ala Ala Leu Val Leu Arg Gly Leu
1               5                   10                  15

Val Lys Asp Gly Asn Phe Ala Ile Lys
            20                  25
```

<210> SEQ ID NO 25
<211> LENGTH: 25
<212> TYPE: PRT
<213> ORGANISM: Borrelia sp.

<400> SEQUENCE: 25

```
Leu Lys Lys Asp Asp Asn Ile Ala Ala Ala Val Val Leu Arg Gly Ile
1               5                   10                  15

Val Lys Asp Gly Asn Phe Ala Ile Lys
            20                  25
```

<210> SEQ ID NO 26
<211> LENGTH: 25
<212> TYPE: PRT
<213> ORGANISM: Borrelia sp.

<400> SEQUENCE: 26

```
Leu Lys Lys Asp Asp Asn Ile Ala Ala Ala Leu Val Leu Arg Gly Ile
1               5                   10                  15

Val Lys Asp Gly Asn Phe Ala Ile Lys
            20                  25
```

<210> SEQ ID NO 27
<211> LENGTH: 25
<212> TYPE: PRT
<213> ORGANISM: Borrelia sp.

<400> SEQUENCE: 27

Leu Lys Lys Asp Asp Asn Ile Ala Ala Ala Val Val Leu Arg Gly Leu
1 5 10 15

Ala Lys Asp Gly Arg Phe Ala Trp Lys
20 25

<210> SEQ ID NO 28
<211> LENGTH: 25
<212> TYPE: PRT
<213> ORGANISM: Borrelia sp.

<400> SEQUENCE: 28

Leu Lys Lys Asp Asp Asn Ile Ala Ala Ala Leu Val Leu Arg Gly Leu
1 5 10 15

Ala Lys Asp Gly Arg Phe Ala Trp Lys
20 25

<210> SEQ ID NO 29
<211> LENGTH: 25
<212> TYPE: PRT
<213> ORGANISM: Borrelia sp.

<400> SEQUENCE: 29

Leu Lys Lys Asp Asp Asn Ile Ala Ala Ala Val Val Leu Arg Gly Ile
1 5 10 15

Ala Lys Asp Gly Arg Phe Ala Trp Lys
20 25

<210> SEQ ID NO 30
<211> LENGTH: 25
<212> TYPE: PRT
<213> ORGANISM: Borrelia sp.

<400> SEQUENCE: 30

Leu Lys Lys Asp Asp Asn Ile Ala Ala Ala Leu Val Leu Arg Gly Ile
1 5 10 15

Ala Lys Asp Gly Arg Phe Ala Trp Lys
20 25

<210> SEQ ID NO 31
<211> LENGTH: 25
<212> TYPE: PRT
<213> ORGANISM: Borrelia sp.

<400> SEQUENCE: 31

Leu Lys Lys Asp Asp Asn Ile Ala Ala Ala Val Val Leu Arg Gly Leu
1 5 10 15

Val Lys Asp Gly Arg Phe Ala Trp Lys
20 25

<210> SEQ ID NO 32
<211> LENGTH: 25
<212> TYPE: PRT
<213> ORGANISM: Borrelia sp.

<400> SEQUENCE: 32

Leu Lys Lys Asp Asp Asn Ile Ala Ala Ala Leu Val Leu Arg Gly Leu
1 5 10 15

Val Lys Asp Gly Arg Phe Ala Trp Lys
20 25

-continued

<210> SEQ ID NO 33
<211> LENGTH: 25
<212> TYPE: PRT
<213> ORGANISM: Borrelia sp.

<400> SEQUENCE: 33

Leu Lys Lys Asp Asp Asn Ile Ala Ala Ala Val Val Leu Arg Gly Ile
1 5 10 15

Val Lys Asp Gly Arg Phe Ala Trp Lys
20 25

<210> SEQ ID NO 34
<211> LENGTH: 25
<212> TYPE: PRT
<213> ORGANISM: Borrelia sp.

<400> SEQUENCE: 34

Leu Lys Lys Asp Asp Asn Ile Ala Ala Ala Leu Val Leu Arg Gly Ile
1 5 10 15

Val Lys Asp Gly Arg Phe Ala Trp Lys
20 25

<210> SEQ ID NO 35
<211> LENGTH: 25
<212> TYPE: PRT
<213> ORGANISM: Borrelia sp.

<400> SEQUENCE: 35

Leu Lys Lys Asp Asp Asn Ile Ala Ala Ala Val Val Leu Arg Gly Leu
1 5 10 15

Ala Lys Asp Gly Asp Phe Ala Trp Lys
20 25

<210> SEQ ID NO 36
<211> LENGTH: 25
<212> TYPE: PRT
<213> ORGANISM: Borrelia sp.

<400> SEQUENCE: 36

Leu Lys Lys Asp Asp Asn Ile Ala Ala Ala Leu Val Leu Arg Gly Leu
1 5 10 15

Ala Lys Asp Gly Asp Phe Ala Trp Lys
20 25

<210> SEQ ID NO 37
<211> LENGTH: 25
<212> TYPE: PRT
<213> ORGANISM: Borrelia sp.

<400> SEQUENCE: 37

Leu Lys Lys Asp Asp Asn Ile Ala Ala Ala Val Val Leu Arg Gly Ile
1 5 10 15

Ala Lys Asp Gly Asp Phe Ala Trp Lys
20 25

<210> SEQ ID NO 38
<211> LENGTH: 25
<212> TYPE: PRT
<213> ORGANISM: Borrelia sp.

<400> SEQUENCE: 38

Leu Lys Lys Asp Asp Asn Ile Ala Ala Ala Leu Val Leu Arg Gly Ile
1 5 10 15

Ala Lys Asp Gly Asp Phe Ala Trp Lys
20 25

<210> SEQ ID NO 39
<211> LENGTH: 25
<212> TYPE: PRT
<213> ORGANISM: Borrelia sp.

<400> SEQUENCE: 39

Leu Lys Lys Asp Asp Asn Ile Ala Ala Ala Val Val Leu Arg Gly Leu
1 5 10 15

Val Lys Asp Gly Asp Phe Ala Trp Lys
20 25

<210> SEQ ID NO 40
<211> LENGTH: 25
<212> TYPE: PRT
<213> ORGANISM: Borrelia sp.

<400> SEQUENCE: 40

Leu Lys Lys Asp Asp Asn Ile Ala Ala Ala Leu Val Leu Arg Gly Leu
1 5 10 15

Val Lys Asp Gly Asp Phe Ala Trp Lys
20 25

<210> SEQ ID NO 41
<211> LENGTH: 25
<212> TYPE: PRT
<213> ORGANISM: Borrelia sp.

<400> SEQUENCE: 41

Leu Lys Lys Asp Asp Asn Ile Ala Ala Ala Val Val Leu Arg Gly Ile
1 5 10 15

Val Lys Asp Gly Asp Phe Ala Trp Lys
20 25

<210> SEQ ID NO 42
<211> LENGTH: 25
<212> TYPE: PRT
<213> ORGANISM: Borrelia sp.

<400> SEQUENCE: 42

Leu Lys Lys Asp Asp Asn Ile Ala Ala Ala Leu Val Leu Arg Gly Ile
1 5 10 15

Val Lys Asp Gly Asp Phe Ala Trp Lys
20 25

<210> SEQ ID NO 43
<211> LENGTH: 25
<212> TYPE: PRT
<213> ORGANISM: Borrelia sp.

<400> SEQUENCE: 43

Leu Lys Lys Asp Asp Asn Ile Ala Ala Ala Val Val Leu Arg Gly Leu
1 5 10 15

Ala Lys Asp Gly Asn Phe Ala Trp Lys
20 25

```
<210> SEQ ID NO 44
<211> LENGTH: 25
<212> TYPE: PRT
<213> ORGANISM: Borrelia sp.

<400> SEQUENCE: 44

Leu Lys Lys Asp Asp Asn Ile Ala Ala Ala Leu Val Leu Arg Gly Leu
1               5                   10                  15

Ala Lys Asp Gly Asn Phe Ala Trp Lys
            20                  25


<210> SEQ ID NO 45
<211> LENGTH: 25
<212> TYPE: PRT
<213> ORGANISM: Borrelia sp.

<400> SEQUENCE: 45

Leu Lys Lys Asp Asp Asn Ile Ala Ala Ala Val Val Leu Arg Gly Ile
1               5                   10                  15

Ala Lys Asp Gly Asn Phe Ala Trp Lys
            20                  25


<210> SEQ ID NO 46
<211> LENGTH: 25
<212> TYPE: PRT
<213> ORGANISM: Borrelia sp.

<400> SEQUENCE: 46

Leu Lys Lys Asp Asp Asn Ile Ala Ala Ala Leu Val Leu Arg Gly Ile
1               5                   10                  15

Ala Lys Asp Gly Asn Phe Ala Trp Lys
            20                  25


<210> SEQ ID NO 47
<211> LENGTH: 25
<212> TYPE: PRT
<213> ORGANISM: Borrelia sp.

<400> SEQUENCE: 47

Leu Lys Lys Asp Asp Asn Ile Ala Ala Ala Val Val Leu Arg Gly Leu
1               5                   10                  15

Val Lys Asp Gly Asn Phe Ala Trp Lys
            20                  25


<210> SEQ ID NO 48
<211> LENGTH: 25
<212> TYPE: PRT
<213> ORGANISM: Borrelia sp.

<400> SEQUENCE: 48

Leu Lys Lys Asp Asp Asn Ile Ala Ala Ala Leu Val Leu Arg Gly Leu
1               5                   10                  15

Val Lys Asp Gly Asn Phe Ala Trp Lys
            20                  25


<210> SEQ ID NO 49
<211> LENGTH: 25
<212> TYPE: PRT
<213> ORGANISM: Borrelia sp.
```

<400> SEQUENCE: 49

Leu Lys Lys Asp Asp Asn Ile Ala Ala Ala Val Val Leu Arg Gly Ile
1 5 10 15

Val Lys Asp Gly Asn Phe Ala Trp Lys
20 25

<210> SEQ ID NO 50
<211> LENGTH: 25
<212> TYPE: PRT
<213> ORGANISM: Borrelia sp.

<400> SEQUENCE: 50

Leu Lys Lys Asp Asp Asn Ile Ala Ala Ala Leu Val Leu Arg Gly Ile
1 5 10 15

Val Lys Asp Gly Asn Phe Ala Trp Lys
20 25

<210> SEQ ID NO 51
<211> LENGTH: 25
<212> TYPE: PRT
<213> ORGANISM: Borrelia sp.

<400> SEQUENCE: 51

Leu Lys Lys Asp Asp Asn Ile Ala Ala Ala Val Val Leu Arg Gly Leu
1 5 10 15

Ala Lys Asp Gly Arg Phe Ala Tyr Lys
20 25

<210> SEQ ID NO 52
<211> LENGTH: 25
<212> TYPE: PRT
<213> ORGANISM: Borrelia sp.

<400> SEQUENCE: 52

Leu Lys Lys Asp Asp Asn Ile Ala Ala Ala Leu Val Leu Arg Gly Leu
1 5 10 15

Ala Lys Asp Gly Arg Phe Ala Tyr Lys
20 25

<210> SEQ ID NO 53
<211> LENGTH: 25
<212> TYPE: PRT
<213> ORGANISM: Borrelia sp.

<400> SEQUENCE: 53

Leu Lys Lys Asp Asp Asn Ile Ala Ala Ala Val Val Leu Arg Gly Ile
1 5 10 15

Ala Lys Asp Gly Arg Phe Ala Tyr Lys
20 25

<210> SEQ ID NO 54
<211> LENGTH: 25
<212> TYPE: PRT
<213> ORGANISM: Borrelia sp.

<400> SEQUENCE: 54

Leu Lys Lys Asp Asp Asn Ile Ala Ala Ala Leu Val Leu Arg Gly Ile
1 5 10 15

Ala Lys Asp Gly Arg Phe Ala Tyr Lys
20 25

<210> SEQ ID NO 55
<211> LENGTH: 25
<212> TYPE: PRT
<213> ORGANISM: Borrelia sp.

<400> SEQUENCE: 55

```
Leu Lys Lys Asp Asp Asn Ile Ala Ala Ala Val Val Leu Arg Gly Leu
1               5                   10                  15

Val Lys Asp Gly Arg Phe Ala Tyr Lys
            20                  25
```

<210> SEQ ID NO 56
<211> LENGTH: 25
<212> TYPE: PRT
<213> ORGANISM: Borrelia sp.

<400> SEQUENCE: 56

```
Leu Lys Lys Asp Asp Asn Ile Ala Ala Ala Leu Val Leu Arg Gly Leu
1               5                   10                  15

Val Lys Asp Gly Arg Phe Ala Tyr Lys
            20                  25
```

<210> SEQ ID NO 57
<211> LENGTH: 25
<212> TYPE: PRT
<213> ORGANISM: Borrelia sp.

<400> SEQUENCE: 57

```
Leu Lys Lys Asp Asp Asn Ile Ala Ala Ala Val Val Leu Arg Gly Ile
1               5                   10                  15

Val Lys Asp Gly Arg Phe Ala Tyr Lys
            20                  25
```

<210> SEQ ID NO 58
<211> LENGTH: 25
<212> TYPE: PRT
<213> ORGANISM: Borrelia sp.

<400> SEQUENCE: 58

```
Leu Lys Lys Asp Asp Asn Ile Ala Ala Ala Leu Val Leu Arg Gly Ile
1               5                   10                  15

Val Lys Asp Gly Arg Phe Ala Tyr Lys
            20                  25
```

<210> SEQ ID NO 59
<211> LENGTH: 25
<212> TYPE: PRT
<213> ORGANISM: Borrelia sp.

<400> SEQUENCE: 59

```
Leu Lys Lys Asp Asp Asn Ile Ala Ala Ala Val Val Leu Arg Gly Leu
1               5                   10                  15

Ala Lys Asp Gly Asp Phe Ala Tyr Lys
            20                  25
```

<210> SEQ ID NO 60
<211> LENGTH: 25
<212> TYPE: PRT
<213> ORGANISM: Borrelia sp.

<400> SEQUENCE: 60

Leu Lys Lys Asp Asp Asn Ile Ala Ala Ala Leu Val Leu Arg Gly Leu
1 5 10 15

Ala Lys Asp Gly Asp Phe Ala Tyr Lys
20 25

<210> SEQ ID NO 61
<211> LENGTH: 25
<212> TYPE: PRT
<213> ORGANISM: Borrelia sp.

<400> SEQUENCE: 61

Leu Lys Lys Asp Asp Asn Ile Ala Ala Ala Val Val Leu Arg Gly Ile
1 5 10 15

Ala Lys Asp Gly Asp Phe Ala Tyr Lys
20 25

<210> SEQ ID NO 62
<211> LENGTH: 25
<212> TYPE: PRT
<213> ORGANISM: Borrelia sp.

<400> SEQUENCE: 62

Leu Lys Lys Asp Asp Asn Ile Ala Ala Ala Leu Val Leu Arg Gly Ile
1 5 10 15

Ala Lys Asp Gly Asp Phe Ala Tyr Lys
20 25

<210> SEQ ID NO 63
<211> LENGTH: 25
<212> TYPE: PRT
<213> ORGANISM: Borrelia sp.

<400> SEQUENCE: 63

Leu Lys Lys Asp Asp Asn Ile Ala Ala Ala Val Val Leu Arg Gly Leu
1 5 10 15

Val Lys Asp Gly Asp Phe Ala Tyr Lys
20 25

<210> SEQ ID NO 64
<211> LENGTH: 25
<212> TYPE: PRT
<213> ORGANISM: Borrelia sp.

<400> SEQUENCE: 64

Leu Lys Lys Asp Asp Asn Ile Ala Ala Ala Leu Val Leu Arg Gly Leu
1 5 10 15

Val Lys Asp Gly Asp Phe Ala Tyr Lys
20 25

<210> SEQ ID NO 65
<211> LENGTH: 25
<212> TYPE: PRT
<213> ORGANISM: Borrelia sp.

<400> SEQUENCE: 65

Leu Lys Lys Asp Asp Asn Ile Ala Ala Ala Val Val Leu Arg Gly Ile
1 5 10 15

Val Lys Asp Gly Asp Phe Ala Tyr Lys
20 25

<210> SEQ ID NO 66
<211> LENGTH: 25
<212> TYPE: PRT
<213> ORGANISM: Borrelia sp.

<400> SEQUENCE: 66

Leu Lys Lys Asp Asp Asn Ile Ala Ala Ala Leu Val Leu Arg Gly Ile
1               5                   10                  15

Val Lys Asp Gly Asp Phe Ala Tyr Lys
            20                  25

<210> SEQ ID NO 67
<211> LENGTH: 25
<212> TYPE: PRT
<213> ORGANISM: Borrelia sp.

<400> SEQUENCE: 67

Leu Lys Lys Asp Asp Asn Ile Ala Ala Ala Val Val Leu Arg Gly Leu
1               5                   10                  15

Ala Lys Asp Gly Asn Phe Ala Tyr Lys
            20                  25

<210> SEQ ID NO 68
<211> LENGTH: 25
<212> TYPE: PRT
<213> ORGANISM: Borrelia sp.

<400> SEQUENCE: 68

Leu Lys Lys Asp Asp Asn Ile Ala Ala Ala Leu Val Leu Arg Gly Leu
1               5                   10                  15

Ala Lys Asp Gly Asn Phe Ala Tyr Lys
            20                  25

<210> SEQ ID NO 69
<211> LENGTH: 25
<212> TYPE: PRT
<213> ORGANISM: Borrelia sp.

<400> SEQUENCE: 69

Leu Lys Lys Asp Asp Asn Ile Ala Ala Ala Val Val Leu Arg Gly Ile
1               5                   10                  15

Ala Lys Asp Gly Asn Phe Ala Tyr Lys
            20                  25

<210> SEQ ID NO 70
<211> LENGTH: 25
<212> TYPE: PRT
<213> ORGANISM: Borrelia sp.

<400> SEQUENCE: 70

Leu Lys Lys Asp Asp Asn Ile Ala Ala Ala Leu Val Leu Arg Gly Ile
1               5                   10                  15

Ala Lys Asp Gly Asn Phe Ala Tyr Lys
            20                  25

<210> SEQ ID NO 71
<211> LENGTH: 25
<212> TYPE: PRT
<213> ORGANISM: Borrelia sp.

<400> SEQUENCE: 71

Leu Lys Lys Asp Asp Asn Ile Ala Ala Ala Val Val Leu Arg Gly Leu
1 5 10 15

Val Lys Asp Gly Asn Phe Ala Tyr Lys
20 25

<210> SEQ ID NO 72
<211> LENGTH: 25
<212> TYPE: PRT
<213> ORGANISM: Borrelia sp.

<400> SEQUENCE: 72

Leu Lys Lys Asp Asp Asn Ile Ala Ala Ala Leu Val Leu Arg Gly Leu
1 5 10 15

Val Lys Asp Gly Asn Phe Ala Tyr Lys
20 25

<210> SEQ ID NO 73
<211> LENGTH: 25
<212> TYPE: PRT
<213> ORGANISM: Borrelia sp.

<400> SEQUENCE: 73

Leu Lys Lys Asp Asp Asn Ile Ala Ala Ala Val Val Leu Arg Gly Ile
1 5 10 15

Val Lys Asp Gly Asn Phe Ala Tyr Lys
20 25

<210> SEQ ID NO 74
<211> LENGTH: 25
<212> TYPE: PRT
<213> ORGANISM: Borrelia sp.

<400> SEQUENCE: 74

Leu Lys Lys Asp Asp Asn Ile Ala Ala Ala Leu Val Leu Arg Gly Ile
1 5 10 15

Val Lys Asp Gly Asn Phe Ala Tyr Lys
20 25

<210> SEQ ID NO 75
<211> LENGTH: 25
<212> TYPE: PRT
<213> ORGANISM: Borrelia sp.

<400> SEQUENCE: 75

Leu Lys Lys Asp Asp Asn Ile Ala Ala Ala Val Val Leu Arg Gly Leu
1 5 10 15

Ala Lys Asp Gly Arg Phe Ala Ile Arg
20 25

<210> SEQ ID NO 76
<211> LENGTH: 25
<212> TYPE: PRT
<213> ORGANISM: Borrelia sp.

<400> SEQUENCE: 76

Leu Lys Lys Asp Asp Asn Ile Ala Ala Ala Leu Val Leu Arg Gly Leu
1 5 10 15

Ala Lys Asp Gly Arg Phe Ala Ile Arg
20 25

<210> SEQ ID NO 77
<211> LENGTH: 25
<212> TYPE: PRT
<213> ORGANISM: Borrelia sp.

<400> SEQUENCE: 77

```
Leu Lys Lys Asp Asp Asn Ile Ala Ala Ala Val Val Leu Arg Gly Ile
1               5                   10                  15

Ala Lys Asp Gly Arg Phe Ala Ile Arg
            20                  25
```

<210> SEQ ID NO 78
<211> LENGTH: 25
<212> TYPE: PRT
<213> ORGANISM: Borrelia sp.

<400> SEQUENCE: 78

```
Leu Lys Lys Asp Asp Asn Ile Ala Ala Ala Leu Val Leu Arg Gly Ile
1               5                   10                  15

Ala Lys Asp Gly Arg Phe Ala Ile Arg
            20                  25
```

<210> SEQ ID NO 79
<211> LENGTH: 25
<212> TYPE: PRT
<213> ORGANISM: Borrelia sp.

<400> SEQUENCE: 79

```
Leu Lys Lys Asp Asp Asn Ile Ala Ala Ala Val Val Leu Arg Gly Leu
1               5                   10                  15

Val Lys Asp Gly Arg Phe Ala Ile Arg
            20                  25
```

<210> SEQ ID NO 80
<211> LENGTH: 25
<212> TYPE: PRT
<213> ORGANISM: Borrelia sp.

<400> SEQUENCE: 80

```
Leu Lys Lys Asp Asp Asn Ile Ala Ala Ala Leu Val Leu Arg Gly Leu
1               5                   10                  15

Val Lys Asp Gly Arg Phe Ala Ile Arg
            20                  25
```

<210> SEQ ID NO 81
<211> LENGTH: 25
<212> TYPE: PRT
<213> ORGANISM: Borrelia sp.

<400> SEQUENCE: 81

```
Leu Lys Lys Asp Asp Asn Ile Ala Ala Ala Val Val Leu Arg Gly Ile
1               5                   10                  15

Val Lys Asp Gly Arg Phe Ala Ile Arg
            20                  25
```

<210> SEQ ID NO 82
<211> LENGTH: 25
<212> TYPE: PRT
<213> ORGANISM: Borrelia sp.

<400> SEQUENCE: 82

Leu Lys Lys Asp Asp Asn Ile Ala Ala Ala Leu Val Leu Arg Gly Ile
1 5 10 15

Val Lys Asp Gly Arg Phe Ala Ile Arg
20 25

<210> SEQ ID NO 83
<211> LENGTH: 25
<212> TYPE: PRT
<213> ORGANISM: Borrelia sp.

<400> SEQUENCE: 83

Leu Lys Lys Asp Asp Asn Ile Ala Ala Ala Val Val Leu Arg Gly Leu
1 5 10 15

Ala Lys Asp Gly Asp Phe Ala Ile Arg
20 25

<210> SEQ ID NO 84
<211> LENGTH: 25
<212> TYPE: PRT
<213> ORGANISM: Borrelia sp.

<400> SEQUENCE: 84

Leu Lys Lys Asp Asp Asn Ile Ala Ala Ala Leu Val Leu Arg Gly Leu
1 5 10 15

Ala Lys Asp Gly Asp Phe Ala Ile Arg
20 25

<210> SEQ ID NO 85
<211> LENGTH: 25
<212> TYPE: PRT
<213> ORGANISM: Borrelia sp.

<400> SEQUENCE: 85

Leu Lys Lys Asp Asp Asn Ile Ala Ala Ala Val Val Leu Arg Gly Ile
1 5 10 15

Ala Lys Asp Gly Asp Phe Ala Ile Arg
20 25

<210> SEQ ID NO 86
<211> LENGTH: 25
<212> TYPE: PRT
<213> ORGANISM: Borrelia sp.

<400> SEQUENCE: 86

Leu Lys Lys Asp Asp Asn Ile Ala Ala Ala Leu Val Leu Arg Gly Ile
1 5 10 15

Ala Lys Asp Gly Asp Phe Ala Ile Arg
20 25

<210> SEQ ID NO 87
<211> LENGTH: 25
<212> TYPE: PRT
<213> ORGANISM: Borrelia sp.

<400> SEQUENCE: 87

Leu Lys Lys Asp Asp Asn Ile Ala Ala Ala Val Val Leu Arg Gly Leu
1 5 10 15

Val Lys Asp Gly Asp Phe Ala Ile Arg
20 25

<210> SEQ ID NO 88
<211> LENGTH: 25
<212> TYPE: PRT
<213> ORGANISM: Borrelia sp.

<400> SEQUENCE: 88

```
Leu Lys Lys Asp Asp Asn Ile Ala Ala Ala Leu Val Leu Arg Gly Leu
1               5                   10                  15

Val Lys Asp Gly Asp Phe Ala Ile Arg
            20                  25
```

<210> SEQ ID NO 89
<211> LENGTH: 25
<212> TYPE: PRT
<213> ORGANISM: Borrelia sp.

<400> SEQUENCE: 89

```
Leu Lys Lys Asp Asp Asn Ile Ala Ala Ala Val Val Leu Arg Gly Ile
1               5                   10                  15

Val Lys Asp Gly Asp Phe Ala Ile Arg
            20                  25
```

<210> SEQ ID NO 90
<211> LENGTH: 25
<212> TYPE: PRT
<213> ORGANISM: Borrelia sp.

<400> SEQUENCE: 90

```
Leu Lys Lys Asp Asp Asn Ile Ala Ala Ala Leu Val Leu Arg Gly Ile
1               5                   10                  15

Val Lys Asp Gly Asp Phe Ala Ile Arg
            20                  25
```

<210> SEQ ID NO 91
<211> LENGTH: 25
<212> TYPE: PRT
<213> ORGANISM: Borrelia sp.

<400> SEQUENCE: 91

```
Leu Lys Lys Asp Asp Asn Ile Ala Ala Ala Val Val Leu Arg Gly Leu
1               5                   10                  15

Ala Lys Asp Gly Asn Phe Ala Ile Arg
            20                  25
```

<210> SEQ ID NO 92
<211> LENGTH: 25
<212> TYPE: PRT
<213> ORGANISM: Borrelia sp.

<400> SEQUENCE: 92

```
Leu Lys Lys Asp Asp Asn Ile Ala Ala Ala Leu Val Leu Arg Gly Leu
1               5                   10                  15

Ala Lys Asp Gly Asn Phe Ala Ile Arg
            20                  25
```

<210> SEQ ID NO 93
<211> LENGTH: 25
<212> TYPE: PRT
<213> ORGANISM: Borrelia sp.

<400> SEQUENCE: 93

Leu Lys Lys Asp Asp Asn Ile Ala Ala Ala Val Val Leu Arg Gly Ile
1 5 10 15

Ala Lys Asp Gly Asn Phe Ala Ile Arg
20 25

<210> SEQ ID NO 94
<211> LENGTH: 25
<212> TYPE: PRT
<213> ORGANISM: Borrelia sp.

<400> SEQUENCE: 94

Leu Lys Lys Asp Asp Asn Ile Ala Ala Ala Leu Val Leu Arg Gly Ile
1 5 10 15

Ala Lys Asp Gly Asn Phe Ala Ile Arg
20 25

<210> SEQ ID NO 95
<211> LENGTH: 25
<212> TYPE: PRT
<213> ORGANISM: Borrelia sp.

<400> SEQUENCE: 95

Leu Lys Lys Asp Asp Asn Ile Ala Ala Ala Val Val Leu Arg Gly Leu
1 5 10 15

Val Lys Asp Gly Asn Phe Ala Ile Arg
20 25

<210> SEQ ID NO 96
<211> LENGTH: 25
<212> TYPE: PRT
<213> ORGANISM: Borrelia sp.

<400> SEQUENCE: 96

Leu Lys Lys Asp Asp Asn Ile Ala Ala Ala Leu Val Leu Arg Gly Leu
1 5 10 15

Val Lys Asp Gly Asn Phe Ala Ile Arg
20 25

<210> SEQ ID NO 97
<211> LENGTH: 25
<212> TYPE: PRT
<213> ORGANISM: Borrelia sp.

<400> SEQUENCE: 97

Leu Lys Lys Asp Asp Asn Ile Ala Ala Ala Val Val Leu Arg Gly Ile
1 5 10 15

Val Lys Asp Gly Asn Phe Ala Ile Arg
20 25

<210> SEQ ID NO 98
<211> LENGTH: 25
<212> TYPE: PRT
<213> ORGANISM: Borrelia sp.

<400> SEQUENCE: 98

Leu Lys Lys Asp Asp Asn Ile Ala Ala Ala Leu Val Leu Arg Gly Ile
1 5 10 15

Val Lys Asp Gly Asn Phe Ala Ile Arg
20 25

<210> SEQ ID NO 99
<211> LENGTH: 25
<212> TYPE: PRT
<213> ORGANISM: Borrelia sp.

<400> SEQUENCE: 99

Leu Lys Lys Asp Asp Asn Ile Ala Ala Ala Val Val Leu Arg Gly Leu
1 5 10 15

Ala Lys Asp Gly Arg Phe Ala Trp Arg
20 25

<210> SEQ ID NO 100
<211> LENGTH: 25
<212> TYPE: PRT
<213> ORGANISM: Borrelia sp.

<400> SEQUENCE: 100

Leu Lys Lys Asp Asp Asn Ile Ala Ala Ala Leu Val Leu Arg Gly Leu
1 5 10 15

Ala Lys Asp Gly Arg Phe Ala Trp Arg
20 25

<210> SEQ ID NO 101
<211> LENGTH: 25
<212> TYPE: PRT
<213> ORGANISM: Borrelia sp.

<400> SEQUENCE: 101

Leu Lys Lys Asp Asp Asn Ile Ala Ala Ala Val Val Leu Arg Gly Ile
1 5 10 15

Ala Lys Asp Gly Arg Phe Ala Trp Arg
20 25

<210> SEQ ID NO 102
<211> LENGTH: 25
<212> TYPE: PRT
<213> ORGANISM: Borrelia sp.

<400> SEQUENCE: 102

Leu Lys Lys Asp Asp Asn Ile Ala Ala Ala Leu Val Leu Arg Gly Ile
1 5 10 15

Ala Lys Asp Gly Arg Phe Ala Trp Arg
20 25

<210> SEQ ID NO 103
<211> LENGTH: 25
<212> TYPE: PRT
<213> ORGANISM: Borrelia sp.

<400> SEQUENCE: 103

Leu Lys Lys Asp Asp Asn Ile Ala Ala Ala Val Val Leu Arg Gly Leu
1 5 10 15

Val Lys Asp Gly Arg Phe Ala Trp Arg
20 25

<210> SEQ ID NO 104
<211> LENGTH: 25
<212> TYPE: PRT
<213> ORGANISM: Borrelia sp.

<400> SEQUENCE: 104

Leu Lys Lys Asp Asp Asn Ile Ala Ala Ala Leu Val Leu Arg Gly Leu
1 5 10 15

Val Lys Asp Gly Arg Phe Ala Trp Arg
20 25

<210> SEQ ID NO 105
<211> LENGTH: 25
<212> TYPE: PRT
<213> ORGANISM: Borrelia sp.

<400> SEQUENCE: 105

Leu Lys Lys Asp Asp Asn Ile Ala Ala Ala Val Val Leu Arg Gly Ile
1 5 10 15

Val Lys Asp Gly Arg Phe Ala Trp Arg
20 25

<210> SEQ ID NO 106
<211> LENGTH: 25
<212> TYPE: PRT
<213> ORGANISM: Borrelia sp.

<400> SEQUENCE: 106

Leu Lys Lys Asp Asp Asn Ile Ala Ala Ala Leu Val Leu Arg Gly Ile
1 5 10 15

Val Lys Asp Gly Arg Phe Ala Trp Arg
20 25

<210> SEQ ID NO 107
<211> LENGTH: 25
<212> TYPE: PRT
<213> ORGANISM: Borrelia sp.

<400> SEQUENCE: 107

Leu Lys Lys Asp Asp Asn Ile Ala Ala Ala Val Val Leu Arg Gly Leu
1 5 10 15

Ala Lys Asp Gly Asp Phe Ala Trp Arg
20 25

<210> SEQ ID NO 108
<211> LENGTH: 25
<212> TYPE: PRT
<213> ORGANISM: Borrelia sp.

<400> SEQUENCE: 108

Leu Lys Lys Asp Asp Asn Ile Ala Ala Ala Leu Val Leu Arg Gly Leu
1 5 10 15

Ala Lys Asp Gly Asp Phe Ala Trp Arg
20 25

<210> SEQ ID NO 109
<211> LENGTH: 25
<212> TYPE: PRT
<213> ORGANISM: Borrelia sp.

<400> SEQUENCE: 109

Leu Lys Lys Asp Asp Asn Ile Ala Ala Ala Val Val Leu Arg Gly Ile
1 5 10 15

Ala Lys Asp Gly Asp Phe Ala Trp Arg
20 25

<210> SEQ ID NO 110
<211> LENGTH: 25
<212> TYPE: PRT
<213> ORGANISM: Borrelia sp.

<400> SEQUENCE: 110

```
Leu Lys Lys Asp Asp Asn Ile Ala Ala Ala Leu Val Leu Arg Gly Ile
1               5                   10                  15

Ala Lys Asp Gly Asp Phe Ala Trp Arg
            20                  25
```

<210> SEQ ID NO 111
<211> LENGTH: 25
<212> TYPE: PRT
<213> ORGANISM: Borrelia sp.

<400> SEQUENCE: 111

```
Leu Lys Lys Asp Asp Asn Ile Ala Ala Ala Val Val Leu Arg Gly Leu
1               5                   10                  15

Val Lys Asp Gly Asp Phe Ala Trp Arg
            20                  25
```

<210> SEQ ID NO 112
<211> LENGTH: 25
<212> TYPE: PRT
<213> ORGANISM: Borrelia sp.

<400> SEQUENCE: 112

```
Leu Lys Lys Asp Asp Asn Ile Ala Ala Ala Leu Val Leu Arg Gly Leu
1               5                   10                  15

Val Lys Asp Gly Asp Phe Ala Trp Arg
            20                  25
```

<210> SEQ ID NO 113
<211> LENGTH: 25
<212> TYPE: PRT
<213> ORGANISM: Borrelia sp.

<400> SEQUENCE: 113

```
Leu Lys Lys Asp Asp Asn Ile Ala Ala Ala Val Val Leu Arg Gly Ile
1               5                   10                  15

Val Lys Asp Gly Asp Phe Ala Trp Arg
            20                  25
```

<210> SEQ ID NO 114
<211> LENGTH: 25
<212> TYPE: PRT
<213> ORGANISM: Borrelia sp.

<400> SEQUENCE: 114

```
Leu Lys Lys Asp Asp Asn Ile Ala Ala Ala Leu Val Leu Arg Gly Ile
1               5                   10                  15

Val Lys Asp Gly Asp Phe Ala Trp Arg
            20                  25
```

<210> SEQ ID NO 115
<211> LENGTH: 25
<212> TYPE: PRT
<213> ORGANISM: Borrelia sp.

<400> SEQUENCE: 115

Leu Lys Lys Asp Asp Asn Ile Ala Ala Ala Val Val Leu Arg Gly Leu
1 5 10 15

Ala Lys Asp Gly Asn Phe Ala Trp Arg
20 25

<210> SEQ ID NO 116
<211> LENGTH: 25
<212> TYPE: PRT
<213> ORGANISM: Borrelia sp.

<400> SEQUENCE: 116

Leu Lys Lys Asp Asp Asn Ile Ala Ala Ala Leu Val Leu Arg Gly Leu
1 5 10 15

Ala Lys Asp Gly Asn Phe Ala Trp Arg
20 25

<210> SEQ ID NO 117
<211> LENGTH: 25
<212> TYPE: PRT
<213> ORGANISM: Borrelia sp.

<400> SEQUENCE: 117

Leu Lys Lys Asp Asp Asn Ile Ala Ala Ala Val Val Leu Arg Gly Ile
1 5 10 15

Ala Lys Asp Gly Asn Phe Ala Trp Arg
20 25

<210> SEQ ID NO 118
<211> LENGTH: 25
<212> TYPE: PRT
<213> ORGANISM: Borrelia sp.

<400> SEQUENCE: 118

Leu Lys Lys Asp Asp Asn Ile Ala Ala Ala Leu Val Leu Arg Gly Ile
1 5 10 15

Ala Lys Asp Gly Asn Phe Ala Trp Arg
20 25

<210> SEQ ID NO 119
<211> LENGTH: 25
<212> TYPE: PRT
<213> ORGANISM: Borrelia sp.

<400> SEQUENCE: 119

Leu Lys Lys Asp Asp Asn Ile Ala Ala Ala Val Val Leu Arg Gly Leu
1 5 10 15

Val Lys Asp Gly Asn Phe Ala Trp Arg
20 25

<210> SEQ ID NO 120
<211> LENGTH: 25
<212> TYPE: PRT
<213> ORGANISM: Borrelia sp.

<400> SEQUENCE: 120

Leu Lys Lys Asp Asp Asn Ile Ala Ala Ala Leu Val Leu Arg Gly Leu
1 5 10 15

Val Lys Asp Gly Asn Phe Ala Trp Arg
20 25

<210> SEQ ID NO 121
<211> LENGTH: 25
<212> TYPE: PRT
<213> ORGANISM: Borrelia sp.

<400> SEQUENCE: 121

Leu Lys Lys Asp Asp Asn Ile Ala Ala Ala Val Val Leu Arg Gly Ile
1 5 10 15

Val Lys Asp Gly Asn Phe Ala Trp Arg
20 25

<210> SEQ ID NO 122
<211> LENGTH: 25
<212> TYPE: PRT
<213> ORGANISM: Borrelia sp.

<400> SEQUENCE: 122

Leu Lys Lys Asp Asp Asn Ile Ala Ala Ala Leu Val Leu Arg Gly Ile
1 5 10 15

Val Lys Asp Gly Asn Phe Ala Trp Arg
20 25

<210> SEQ ID NO 123
<211> LENGTH: 25
<212> TYPE: PRT
<213> ORGANISM: Borrelia sp.

<400> SEQUENCE: 123

Leu Lys Lys Asp Asp Asn Ile Ala Ala Ala Val Val Leu Arg Gly Leu
1 5 10 15

Ala Lys Asp Gly Arg Phe Ala Tyr Arg
20 25

<210> SEQ ID NO 124
<211> LENGTH: 25
<212> TYPE: PRT
<213> ORGANISM: Borrelia sp.

<400> SEQUENCE: 124

Leu Lys Lys Asp Asp Asn Ile Ala Ala Ala Leu Val Leu Arg Gly Leu
1 5 10 15

Ala Lys Asp Gly Arg Phe Ala Tyr Arg
20 25

<210> SEQ ID NO 125
<211> LENGTH: 25
<212> TYPE: PRT
<213> ORGANISM: Borrelia sp.

<400> SEQUENCE: 125

Leu Lys Lys Asp Asp Asn Ile Ala Ala Ala Val Val Leu Arg Gly Ile
1 5 10 15

Ala Lys Asp Gly Arg Phe Ala Tyr Arg
20 25

<210> SEQ ID NO 126
<211> LENGTH: 25
<212> TYPE: PRT
<213> ORGANISM: Borrelia sp.

<400> SEQUENCE: 126

Leu Lys Lys Asp Asp Asn Ile Ala Ala Ala Leu Val Leu Arg Gly Ile
1 5 10 15

Ala Lys Asp Gly Arg Phe Ala Tyr Arg
20 25

<210> SEQ ID NO 127
<211> LENGTH: 25
<212> TYPE: PRT
<213> ORGANISM: Borrelia sp.

<400> SEQUENCE: 127

Leu Lys Lys Asp Asp Asn Ile Ala Ala Ala Val Val Leu Arg Gly Leu
1 5 10 15

Val Lys Asp Gly Arg Phe Ala Tyr Arg
20 25

<210> SEQ ID NO 128
<211> LENGTH: 25
<212> TYPE: PRT
<213> ORGANISM: Borrelia sp.

<400> SEQUENCE: 128

Leu Lys Lys Asp Asp Asn Ile Ala Ala Ala Leu Val Leu Arg Gly Leu
1 5 10 15

Val Lys Asp Gly Arg Phe Ala Tyr Arg
20 25

<210> SEQ ID NO 129
<211> LENGTH: 25
<212> TYPE: PRT
<213> ORGANISM: Borrelia sp.

<400> SEQUENCE: 129

Leu Lys Lys Asp Asp Asn Ile Ala Ala Ala Val Val Leu Arg Gly Ile
1 5 10 15

Val Lys Asp Gly Arg Phe Ala Tyr Arg
20 25

<210> SEQ ID NO 130
<211> LENGTH: 25
<212> TYPE: PRT
<213> ORGANISM: Borrelia sp.

<400> SEQUENCE: 130

Leu Lys Lys Asp Asp Asn Ile Ala Ala Ala Leu Val Leu Arg Gly Ile
1 5 10 15

Val Lys Asp Gly Arg Phe Ala Tyr Arg
20 25

<210> SEQ ID NO 131
<211> LENGTH: 25
<212> TYPE: PRT
<213> ORGANISM: Borrelia sp.

<400> SEQUENCE: 131

Leu Lys Lys Asp Asp Asn Ile Ala Ala Ala Val Val Leu Arg Gly Leu
1 5 10 15

Ala Lys Asp Gly Asp Phe Ala Tyr Arg
20 25

<210> SEQ ID NO 132
<211> LENGTH: 25
<212> TYPE: PRT
<213> ORGANISM: Borrelia sp.

<400> SEQUENCE: 132

Leu Lys Lys Asp Asp Asn Ile Ala Ala Ala Leu Val Leu Arg Gly Leu
1               5                   10                  15

Ala Lys Asp Gly Asp Phe Ala Tyr Arg
            20                  25

<210> SEQ ID NO 133
<211> LENGTH: 25
<212> TYPE: PRT
<213> ORGANISM: Borrelia sp.

<400> SEQUENCE: 133

Leu Lys Lys Asp Asp Asn Ile Ala Ala Ala Val Val Leu Arg Gly Ile
1               5                   10                  15

Ala Lys Asp Gly Asp Phe Ala Tyr Arg
            20                  25

<210> SEQ ID NO 134
<211> LENGTH: 25
<212> TYPE: PRT
<213> ORGANISM: Borrelia sp.

<400> SEQUENCE: 134

Leu Lys Lys Asp Asp Asn Ile Ala Ala Ala Leu Val Leu Arg Gly Ile
1               5                   10                  15

Ala Lys Asp Gly Asp Phe Ala Tyr Arg
            20                  25

<210> SEQ ID NO 135
<211> LENGTH: 25
<212> TYPE: PRT
<213> ORGANISM: Borrelia sp.

<400> SEQUENCE: 135

Leu Lys Lys Asp Asp Asn Ile Ala Ala Ala Val Val Leu Arg Gly Leu
1               5                   10                  15

Val Lys Asp Gly Asp Phe Ala Tyr Arg
            20                  25

<210> SEQ ID NO 136
<211> LENGTH: 25
<212> TYPE: PRT
<213> ORGANISM: Borrelia sp.

<400> SEQUENCE: 136

Leu Lys Lys Asp Asp Asn Ile Ala Ala Ala Leu Val Leu Arg Gly Leu
1               5                   10                  15

Val Lys Asp Gly Asp Phe Ala Tyr Arg
            20                  25

<210> SEQ ID NO 137
<211> LENGTH: 25
<212> TYPE: PRT
<213> ORGANISM: Borrelia sp.

<400> SEQUENCE: 137

```
Leu Lys Lys Asp Asp Asn Ile Ala Ala Ala Val Val Leu Arg Gly Ile
1               5                   10                  15

Val Lys Asp Gly Asp Phe Ala Tyr Arg
            20                  25
```

<210> SEQ ID NO 138
<211> LENGTH: 25
<212> TYPE: PRT
<213> ORGANISM: Borrelia sp.

<400> SEQUENCE: 138

```
Leu Lys Lys Asp Asp Asn Ile Ala Ala Ala Leu Val Leu Arg Gly Ile
1               5                   10                  15

Val Lys Asp Gly Asp Phe Ala Tyr Arg
            20                  25
```

<210> SEQ ID NO 139
<211> LENGTH: 25
<212> TYPE: PRT
<213> ORGANISM: Borrelia sp.

<400> SEQUENCE: 139

```
Leu Lys Lys Asp Asp Asn Ile Ala Ala Ala Val Val Leu Arg Gly Leu
1               5                   10                  15

Ala Lys Asp Gly Asn Phe Ala Tyr Arg
            20                  25
```

<210> SEQ ID NO 140
<211> LENGTH: 25
<212> TYPE: PRT
<213> ORGANISM: Borrelia sp.

<400> SEQUENCE: 140

```
Leu Lys Lys Asp Asp Asn Ile Ala Ala Ala Leu Val Leu Arg Gly Leu
1               5                   10                  15

Ala Lys Asp Gly Asn Phe Ala Tyr Arg
            20                  25
```

<210> SEQ ID NO 141
<211> LENGTH: 25
<212> TYPE: PRT
<213> ORGANISM: Borrelia sp.

<400> SEQUENCE: 141

```
Leu Lys Lys Asp Asp Asn Ile Ala Ala Ala Val Val Leu Arg Gly Ile
1               5                   10                  15

Ala Lys Asp Gly Asn Phe Ala Tyr Arg
            20                  25
```

<210> SEQ ID NO 142
<211> LENGTH: 25
<212> TYPE: PRT
<213> ORGANISM: Borrelia sp.

<400> SEQUENCE: 142

```
Leu Lys Lys Asp Asp Asn Ile Ala Ala Ala Leu Val Leu Arg Gly Ile
1               5                   10                  15

Ala Lys Asp Gly Asn Phe Ala Tyr Arg
            20                  25
```

<210> SEQ ID NO 143
<211> LENGTH: 25
<212> TYPE: PRT
<213> ORGANISM: Borrelia sp.

<400> SEQUENCE: 143

Leu Lys Lys Asp Asp Asn Ile Ala Ala Ala Val Val Leu Arg Gly Leu
1 5 10 15

Val Lys Asp Gly Asn Phe Ala Tyr Arg
20 25

<210> SEQ ID NO 144
<211> LENGTH: 25
<212> TYPE: PRT
<213> ORGANISM: Borrelia sp.

<400> SEQUENCE: 144

Leu Lys Lys Asp Asp Asn Ile Ala Ala Ala Leu Val Leu Arg Gly Leu
1 5 10 15

Val Lys Asp Gly Asn Phe Ala Tyr Arg
20 25

<210> SEQ ID NO 145
<211> LENGTH: 25
<212> TYPE: PRT
<213> ORGANISM: Borrelia sp.

<400> SEQUENCE: 145

Leu Lys Lys Asp Asp Asn Ile Ala Ala Ala Val Val Leu Arg Gly Ile
1 5 10 15

Val Lys Asp Gly Asn Phe Ala Tyr Arg
20 25

<210> SEQ ID NO 146
<211> LENGTH: 25
<212> TYPE: PRT
<213> ORGANISM: Borrelia sp.

<400> SEQUENCE: 146

Leu Lys Lys Asp Asp Asn Ile Ala Ala Ala Leu Val Leu Arg Gly Ile
1 5 10 15

Val Lys Asp Gly Asn Phe Ala Tyr Arg
20 25

<210> SEQ ID NO 147
<211> LENGTH: 10
<212> TYPE: PRT
<213> ORGANISM: Borrelia sp.

<400> SEQUENCE: 147

Pro Val Val Ala Glu Ser Pro Lys Lys Pro
1 5 10

<210> SEQ ID NO 148
<211> LENGTH: 14
<212> TYPE: PRT
<213> ORGANISM: Borrelia sp.

<400> SEQUENCE: 148

Ile Leu Met Thr Leu Phe Leu Phe Ile Ser Cys Asn Asn Ser
1 5 10

-continued

<210> SEQ ID NO 149
<211> LENGTH: 7
<212> TYPE: PRT
<213> ORGANISM: Borrelia sp.
<220> FEATURE:
<221> NAME/KEY: MISC_FEATURE
<222> LOCATION: (1)..(1)
<223> OTHER INFORMATION: Xaa may be Ala or Val
<220> FEATURE:
<221> NAME/KEY: MISC_FEATURE
<222> LOCATION: (2)..(2)
<223> OTHER INFORMATION: Xaa may be Glu or Asp
<220> FEATURE:
<221> NAME/KEY: MISC_FEATURE
<222> LOCATION: (5)..(5)
<223> OTHER INFORMATION: Xaa may be Lys or Arg
<220> FEATURE:
<221> NAME/KEY: MISC_FEATURE
<222> LOCATION: (6)..(6)
<223> OTHER INFORMATION: Xaa may be Lys or Arg

<400> SEQUENCE: 149

Xaa Xaa Ser Pro Xaa Xaa Pro
1               5

<210> SEQ ID NO 150
<211> LENGTH: 15
<212> TYPE: PRT
<213> ORGANISM: Borrelia sp.
<220> FEATURE:
<221> NAME/KEY: MISC_FEATURE
<222> LOCATION: (2)..(2)
<223> OTHER INFORMATION: Xaa may be Gln or Arg
<220> FEATURE:
<221> NAME/KEY: MISC_FEATURE
<222> LOCATION: (5)..(5)
<223> OTHER INFORMATION: Xaa may be Val or Ala

<400> SEQUENCE: 150

Val Xaa Glu Gly Xaa Gln Gln Glu Gly Ala Gln Gln Pro Ser Cys
1               5                   10                  15

<210> SEQ ID NO 151
<211> LENGTH: 16
<212> TYPE: PRT
<213> ORGANISM: Borrelia sp.
<220> FEATURE:
<221> NAME/KEY: MISC_FEATURE
<222> LOCATION: (3)..(3)
<223> OTHER INFORMATION: Xaa may be Gln or Arg
<220> FEATURE:
<221> NAME/KEY: MISC_FEATURE
<222> LOCATION: (6)..(6)
<223> OTHER INFORMATION: Xaa may be Val or Ala

<400> SEQUENCE: 151

Ala Val Xaa Glu Gly Xaa Gln Gln Glu Gly Ala Gln Gln Pro Ser Cys
1               5                   10                  15

<210> SEQ ID NO 152
<211> LENGTH: 6
<212> TYPE: PRT
<213> ORGANISM: Artificial Sequence
<220> FEATURE:
<223> OTHER INFORMATION: 6X His tag

<400> SEQUENCE: 152

His His His His His His
1               5

PEPTIDES AND METHODS FOR THE DETECTION OF LYME DISEASE ANTIBODIES

CROSS-REFERENCE TO RELATED APPLICATIONS

This application is a divisional of U.S. patent application Ser. No. 14/924,358, filed Oct. 27, 2015, which is a continuation of U.S. patent application Ser. No. 14/304,809, filed Jun. 13, 2014, which issued as U.S. Pat. No. 9,201,071 on Dec. 1, 2015, which is a continuation of U.S. patent application Ser. No. 13/667,909, filed Nov. 2, 2012, which issued as U.S. Pat. No. 8,758,772 on Jun. 24, 2014, which claims the benefit of U.S. Provisional Application No. 61/556,061, filed Nov. 4, 2011; all of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ABAX_039_04US_SeqList_ST25.txt, date recorded: Aug. 23, 2017, file size 45 kilobytes).

BACKGROUND OF THE INVENTION

Lyme disease is a debilitating condition that has become a significant public health concern. The disease is caused by infection with a pathogenic *Borrelia* bacterium (a spirochete) and is transmitted by the bite of various species of *Borrelia*-infected *Ixodes* ticks. Accurate and early detection of Lyme disease is critical to effective treatment. The only clinical symptom sufficient for diagnosis of Lyme disease is the presence of erythema migrans, a rash having a distinctive bulls-eye appearance. However, erythema migrans is only present early during infection and, even then, does not appear in all infected individuals. Other clinical symptoms that have been associated with Lyme disease, such as Bell's palsy, are not specific enough, either alone or in combination, to determine clinical diagnosis in the absence of erythema migrans.

In the absence of erythema migrans, the basis for diagnosis of Lyme disease is an antibody response to a pathogenic *Borrelia* species, such as *Borrelia burgdorferi, Borrelia afzelli*, or *Borrelia garinii*. In North America, the Center for Disease Control (CDC) recommends a two-tier approach for serodiagnosis of Lyme disease consisting of a sensitive first-tier assay, such as ELISA, followed by a western blot if the first tier assay is positive or equivocal. First tier assays have traditionally made use of a whole-cell *Borrelia burgdorferi* antigen or recombinant *Borrelia* proteins. Such assays can be difficult to interpret, though, and are complicated by *Borrelia* antibodies arising from vaccination rather than infection. In addition, whole cell sonicates used in some *Borrelia* assays react with *Treponema* antibodies.

More recently, the C6 peptide assay, based on the conserved IR6 domain of the variable surface antigen (VlsE) of *Borrelia*, has become widely accepted as a first-tier assay having a high degree of sensitivity for disseminated and late Lyme disease. The C6 peptide assay uses a single 25 amino acid sequence of the *Borrelia burgdorferi* VlsE protein as the test antigen. Although it has been suggested that the C6 peptide assay may be suitable for a single-tier approach to diagnosis of Lyme disease, it is becoming apparent that the C6 assay is not sufficiently sensitive for such purposes because it fails to detect certain strains of infectious *Borrelia*.

Accordingly, there remains a need in the art for additional assays for detecting *Borrelia* antigens and serodiagnosis of Lyme disease.

SUMMARY OF THE INVENTION

The present invention is based, in part, on the discovery that certain sequence variants in the IR6 domain of the *Borrelia* VlsE protein provide for robust detection of an antibody response against a wide range of *Borrelia* species. Accordingly, the invention provides compositions, devices, methods, and kits useful for the detection of antibodies that bind to *Borrelia* antigens and the diagnosis of Lyme disease.

In one aspect, the invention provides peptides capable of binding to antibodies that recognize *Borrelia* antigens. In certain embodiments, the peptides comprise a VlsE IR6 domain and a sequence from at least one (e.g., two, three, etc.) other *Borrelia* antigen. In certain embodiments, the at least one other *Borrelia* antigen is a surface antigen (e.g., OspC, p41, or a combination thereof).

In certain embodiments, peptides of the invention comprise a sequence of SEQ ID NO: 1, L-K-K-D-D-N-I-A-A-A-$X_{11}$-V-L-R-G-$X_{16}$-$X_{17}$-K-D-G-$X_{21}$-F-A-$X_{24}$-$X_{25}$ (SEQ ID NO: 1) wherein $X_{11}$ is an amino acid selected from the group consisting of V and L, $X_{16}$ is an amino acid selected from the group consisting of L and I, $X_{17}$ is an amino acid selected from the group consisting of A and V, $X_{21}$ is an amino acid selected from the group consisting of R, D and N, $X_{24}$ is an amino acid selected from the group consisting of I, W, and Y, and $X_{25}$ is an amino acid selected from the group consisting of K and R.

In certain embodiments, peptides of the invention comprise a sequence of SEQ ID NO: 1 and further comprise an additional N-terminal peptide sequence. The additional N-terminal peptide sequence can comprise 1, 2, 3, 4, 5, 6, 7, 8, 9, 10, or more amino acids and can be either a native or non-native sequence. In certain embodiments, peptides of the invention comprise a sequence defined by SEQ ID NO: 1 and further comprise an additional C-terminal sequence. The additional C-terminal peptide sequence can comprise 1, 2, 3, 4, 5, 6, 7, 8, 9, 10, or more amino acids and can be either a native or non-native sequence. In certain embodiments, the non-native sequence comprises a non-VlsE *Borrelia* antigen (e.g., a *Borrelia* OspC or p41 antigen).

In other embodiments, the peptides of the invention comprise a sequence of SEQ ID NO: 2, $n_1$-$n_2$-S-P-$n_5$-$n_6$-P-L-K-K-D-D-N-I-A-A-A-$X_{18}$-V-L-R-G-$X_{23}$-$X_{24}$-K-D-G-$X_{28}$-F-A-$X_{31}$-$X_{32}$-A-V-$c_{35}$-E-G-$c_{38}$-Q-Q-E-G-A-Q-Q-P-S-C (SEQ ID NO: 2) wherein $n_1$ is an amino acid selected from the group consisting of A and V, $n_2$ is an amino acid selected from the group consisting of E and D, $n_5$ is an amino acid selected from the group consisting of K and R, $n_6$ is an amino acid selected from the group consisting of K and R, $X_{18}$ is an amino acid selected from the group consisting of V and L, $X_{23}$ is an amino acid selected from the group consisting of L and I, $X_{24}$ is an amino acid selected from the group consisting of A and V, $X_{28}$ is an amino acid selected from the group consisting of R, D and N, $X_{31}$ is an amino acid selected from the group consisting of I, W, and Y, $X_{32}$ is an amino acid selected from the group consisting of K, and R, $c_{35}$ is an amino acid selected from the group consisting of Q and R, and $c_{38}$ is an amino acid selected from the group consisting of V and A.

In certain embodiments, peptides of the invention comprise at least 25, 30, 35, 40, 45, or more amino acids. In certain embodiments, peptides of the invention are isolated (e.g., synthetic and/or purified) peptides. In certain embodiments, peptides of the invention are conjugated to a ligand. For example, in certain embodiments, the peptides are biotinylated. In other embodiments, the peptides are conjugated to avidin, streptavidin, or neutravidin. In other embodiments, the peptides are conjugated to a carrier protein (e.g., serum albumin, keyhole limpet hemocyanin (KLH), or an immunoglobulin Fc domain). In still other embodiments, the peptides are conjugated to a dendrimer and/or part of a multiple antigenic peptides system (MAPS).

In certain embodiments, peptides of the invention are attached to or immobilized on a solid support. In certain embodiments, the solid support is a bead (e.g., a colloidal particle, nanoparticle, latex bead, etc.), a flow path in a lateral flow immunoassay device (e.g., a porous membrane), a flow path in an analytical rotor, or a tube or well (e.g., in a plate suitable for an ELISA assay).

In another aspect, the invention provides compositions comprising one or more peptides of the invention. For example, in certain embodiments, the invention provides a composition comprising a peptide comprising a sequence of SEQ ID NO: 1, a peptide comprising a sequence of SEQ ID NO: 2, or mixtures thereof. In certain embodiments, the composition comprises a mixture of two, three, four, or more different peptides of the invention, wherein each peptide comprises a sequence of SEQ ID NO: 1 or SEQ ID NO: 2.

In certain embodiments, the peptides are conjugated to a ligand or a signaling moiety. For example, in certain embodiments, the peptides are biotinylated. In other embodiments, the peptides are conjugated to avidin, streptavidin, or neutravidin. In other embodiments, the peptides are conjugated to a carrier protein (e.g., serum albumin, keyhole limpet hemocyanin (KLH), or an immunoglobulin Fc domain). In still other embodiments, the peptides are conjugated to a dendrimer and/or are part of a multiple antigenic peptides system (MAPS).

In another aspect, the invention provides nucleic acids comprising a sequence encoding a peptide of the invention. In addition, the invention provides vectors comprising such nucleic acids, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

In another aspect, the invention provides devices. In certain embodiments, the devices are useful for performing an immunoassay. For example, in certain embodiments, the device is a lateral flow immunoassay device. In other embodiments, the device is an analytical rotor. In other embodiments, the device is a tube or a well, e.g., in a plate suitable for an ELISA assay. In still other embodiments, the device is an electrochemical, optical, or opto-electronic sensor.

In certain embodiments, the device comprises a peptide of the invention. In other embodiments, the device comprises a mixture of different peptides of the invention. For example, in certain embodiments, the device comprises two, three, four, or more different peptides of the invention. In certain embodiments, the peptide or each peptide in the mixture comprises a sequence of SEQ ID NO: 1 or SEQ ID NO: 2. In certain embodiments, the peptides are attached to or immobilized upon the device.

In another aspect, the invention provides methods of detecting in a sample an antibody to an epitope of a *Borrelia* antigen. In certain embodiments, the methods comprise contacting a sample with a peptide of the invention, and detecting formation of an antibody-peptide complex comprising said peptide, wherein formation of said complex is indicative of the presence of an antibody to an epitope of a *Borrelia* antigen in said sample. In certain embodiments, the *Borrelia* antigen is from an infectious *Borrelia* species, such as *Borrelia burgdorferi, Borrelia afzelli*, or *Borrelia garinii*. In certain embodiments, the methods comprise contacting the sample with a mixture of two, three, four, or more different peptides of the invention.

In certain embodiments, the peptide or each peptide in the mixture is an isolated (e.g., synthetic and/or purified) peptide. In certain embodiments, the peptide or mixture of peptides is attached to or immobilized upon a solid support. In certain embodiments, the solid support is a bead (e.g., a colloidal particle, nanoparticle, latex bead, etc.), a flow path in a lateral flow immunoassay device (e.g., a porous membrane), a flow path in an analytical rotor, or a tube or a well (e.g., in a plate suitable for an ELISA assay). In certain embodiments, the solid support comprises metal, glass, a cellulose-based material (e.g., nitrocellulose), or a polymer (e.g., polystyrene, polyethylene, polypropylene, polyester, nylon, polysulfone, etc.). In certain embodiments, the peptide or mixture of different peptides is attached to a dendrimer and/or incorporated into a MAPS system. In certain other embodiments, the peptide or mixture of different peptides is attached to BSA.

In certain embodiments, the detecting step comprises performing an ELISA assay. In other embodiments, the detecting step comprises performing a lateral flow immunoassay. In other embodiments, the detecting step comprises performing an agglutination assay. In other embodiments, the detecting step comprises spinning the sample in an analytical rotor. In other embodiments, the detecting step comprises analyzing the sample using a Western blot, a slot blot, or a dot blot. In still other embodiments, the detecting step comprises analyzing the sample with an electrochemical sensor, an optical sensor, or an opto-electronic sensor.

In certain embodiments, the sample is a bodily fluid, such as blood, serum, plasma, cerebral spinal fluid, urine, mucus, or saliva. In other embodiments, the sample is a tissue (e.g., a tissue homogenate) or a cell lysate. In certain embodiments, the sample is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human.

In another aspect, the invention provides methods of diagnosing Lyme disease in a subject. In certain embodiments, the methods comprise contacting a sample from the subject with a peptide of the invention, and detecting formation of an antibody-peptide complex comprising said peptide, wherein formation of said complex is indicative of the subject having Lyme disease. In certain embodiments, the methods comprise contacting the sample with a mixture of two, three, four, or more different peptides of the invention.

In certain embodiments, the peptide or each peptide in the mixture is an isolated (e.g., synthetic and/or purified) peptide. In certain embodiments, the peptide or mixture of different peptides is attached to or immobilized upon a solid support. For example, in certain embodiments, the solid support is a bead (e.g., a colloidal particle, nanoparticle, latex bead, etc.), a flow path in a lateral flow immunoassay device (e.g., a porous membrane), a flow path in an analytical rotor, or a tube or a well (e.g., in a plate suitable for an ELISA assay). In certain embodiments, the solid support comprises metal, glass, a cellulose-based material (e.g., nitrocellulose), or a polymer (e.g., polystyrene, polyethylene, polypropylene, polyester, nylon, polysulfone, etc.). In certain embodiments, the peptide or mixture of different peptides is attached to a dendrimer and/or incorporated into a MAPS system. In certain other embodiments, the peptide or mixture of different peptides is attached to BSA.

In certain embodiments, the detecting step comprises performing an ELISA assay. In other embodiments, the detecting step comprises performing a lateral flow immunoassay. In other embodiments, the detecting step comprises performing an agglutination assay. In other embodiments, the detecting step comprises spinning the sample in an analytical rotor. In other embodiments, the detecting step comprises analyzing the sample using a Western blot, a slot blot, or a dot blot. In still other embodiments, the detecting step comprises analyzing the sample with an electrochemical sensor, optical sensor, or opto-electronic sensor.

In certain embodiments, the sample is a bodily fluid, such as blood, serum, plasma, cerebral spinal fluid, urine, or saliva. In other embodiments, the sample is a tissue (e.g., a tissue homogenate) or a cell lysate. In certain embodiments, the subject is a wild animal (e.g., a deer or rodent, such as a mouse, chipmunk, squirrel, etc.). In other embodiments, the subject is a lab animal (e.g., a mouse, rat, guinea pig, rabbit, monkey, primate, etc.). In other embodiments, the subject is a domesticated or feral animal (e.g., a dog, a cat, a horse). In still other embodiments, the subject is a human.

In yet another aspect, the invention provides kits. In certain embodiments, the kits comprise a peptide of the invention. In certain embodiments, the kits comprise two, three, four, or more different peptides of the invention. The peptides can comprise a sequence of SEQ ID NO: 1 or SEQ ID NO: 2. In certain embodiments, the peptides are attached to or immobilized on a solid support. For example, in certain embodiments, the solid support is a bead (e.g., a colloidal particle, nanoparticle, latex bead, etc.), a flow path in a lateral flow immunoassay device, a flow path in an analytical rotor, or a tube or a well (e.g., in a plate). In certain embodiments, the peptide or mixture of different peptides is attached to a dendrimer and/or incorporated into a MAPS system. In certain other embodiments, the peptide or mixture of different peptides is attached to BSA.

In certain embodiments, the kits further comprise a population of beads or a plate (e.g., a plate suitable for an ELISA assay). In other embodiments, the kits further comprise a device, such as a lateral flow immunoassay device, an analytical rotor, a Western blot, a dot blot, a slot blot, an electrochemical sensor, an optical sensor, or an opto-electronic sensor. In certain embodiments, the population of beads, the plate, or the device is useful for performing an immunoassay. For example, in certain embodiments, the population of beads, the plate, or the device is useful for detecting formation of an antibody-peptide complex comprising an antibody from a sample and a peptide of the invention. In certain embodiments, a peptide or a mixture of different peptides of the invention is attached to or immobilized on the beads, the plate, or the device.

In certain embodiments, the kits further comprise an instruction. For example, in certain embodiments, the kits comprise an instruction indicating how to use a peptide of the invention to detect an antibody to a *Borrelia* antigen or to diagnose Lyme disease. In certain embodiments, the kits comprise an instruction indicating how to use a population of beads, a plate, or a device (e.g., comprising a peptide or a mixture of different peptides of the invention) to detect an antibody to a *Borrelia* antigen or to diagnose Lyme disease.

Additional aspects and embodiments of the invention will be apparent from the detailed description that follows.

DETAILED DESCRIPTION

Figure 1:
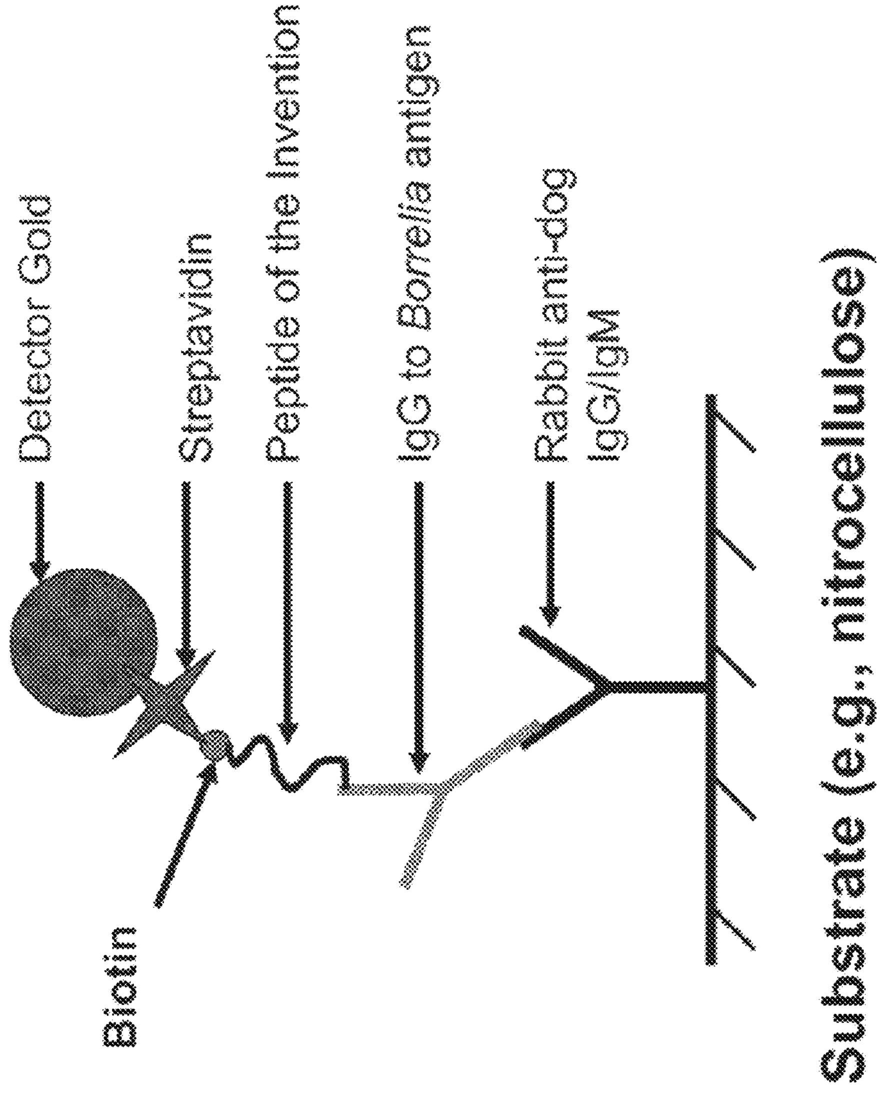
FIG. 1 is a diagram of an indirect sandwich assay which can be used to detect antibodies to *Borrelia* antigens. In this embodiment, anti-human IgG/IgM or anti-dog IgG/IgM antibodies are immobilized to a suitable substrate (e.g., nitrocellulose membrane) at a test site. Antibodies in a test sample are bound by the immobilized antibodies. Test sample antibodies to appropriate *Borrelia* antigens will then bind to peptides of the invention. When the peptides of the invention are conjugated to biotin, colloidal gold-labeled streptavidin can be used to detect the presence of the peptides at the test site. It can be appreciated that the indirect sandwich assay can be operated in the reverse—that is the peptides of the invention can be immobilized to a substrate to capture anti-*Borrelia* antibodies in a test sample and anti-human IgG/IgM or anti-dog IgG/IgM antibodies conjugated to a label (e.g. colloidal gold) can be used to detect the presence of the antibodies bound to the immobilized peptides at the test site.

As used herein, the following terms shall have the following meanings:

The term "antigen," as used herein, refers to a molecule capable of being recognized by an antibody. An antigen can be, for example, a peptide or a modified form thereof. An antigen can comprise one or more epitopes.

The term "epitope," as used herein, is a portion of an antigen that is specifically recognized by an antibody. An epitope, for example, can comprise or consist of a portion of a peptide (e.g., a peptide of the invention). An epitope can be a linear epitope, sequential epitope, or a conformational epitope. In certain embodiments, epitopes may comprise non-contiguous regions.

The terms "nucleic acid," "oligonucleotide" and "polynucleotide" are used interchangeably herein and encompass DNA, RNA, cDNA, whether single stranded or double stranded, as well as chemical modifications thereof.

Single letter amino acid abbreviations used herein have their standard meaning in the art, and all peptide sequences described herein are written according to convention, with the N-terminal end to the left and the C-terminal end to the right.

Additional terms shall be defined, as required, in the detailed description that follows.

Compositions and Devices

The present invention is based, in part, on the discovery that certain sequence variants in the IR6 domain of the *Borrelia* VlsE protein provide for robust detection of an antibody response against a wide range of *Borrelia* species. Accordingly, in one aspect, the invention provides peptides capable of binding to antibodies that recognize *Borrelia* antigens.

In certain embodiments, peptides of the invention comprise a VlsE IR6 domain, or a fragment thereof, and a sequence (e.g., a sequence comprising an epitope) from at least one (e.g., two, three, etc.) other *Borrelia* antigen. In certain embodiments, the at least one other *Borrelia* antigen is a surface antigen or an antigen selected from the group consisting of OspA, OspB, OspC, p41, and combinations thereof. Thus, for example, in certain embodiments, peptides of the invention comprise (i) a VlsE IR6 domain, or a fragment thereof, and (ii) a sequence comprising an epitope of an OspA protein, a sequence comprising an epitope of an OspB protein, a sequence comprising an epitope of an OspC protein, a sequence comprising an epitope of a p41 protein, or a combination of such sequences. In other embodiments, peptides of the invention comprise (i) a VlsE IR6 domain, or a fragment thereof, (ii) a sequence comprising an epitope of an OspC protein, and (iii) a sequence comprising an epitope of a p41 protein.

In certain embodiments, peptides of the invention comprise or consist of a sequence of SEQ ID NO: 1, L-K-K-D-D-N-I-A-A-A-$X_{11}$-V-L-R-G-$X_{16}$-$X_{17}$-K-D-G-$X_{21}$-F-A-$X_{24}$-$X_{25}$ (SEQ ID NO: 1) wherein $X_{11}$ is an amino acid selected from the group consisting of V and L, $X_{16}$ is an amino acid selected from the group consisting of L and I, $X_{17}$ is an amino acid selected from the group consisting of A and V, $X_{21}$ is an amino acid selected from the group consisting of R, D and N, $X_{24}$ is an amino acid selected from the group consisting of I, W, and Y, and $X_{25}$ is an amino acid selected from the group consisting of K and R.

In certain embodiments, a peptide of the invention comprises or consists of the sequence L-K-K-D-D-N-I-A-A-A-V-V-L-R-G-L-A-K-D-G-R-F-A-I-K (SEQ ID NO: 3); L-K-K-D-D-N-I-A-A-A-L-V-L-R-G-L-A-K-D-G-R-F-A-I-K (SEQ ID NO: 4); L-K-K-D-D-N-I-A-A-A-V-V-L-R-G-I-A-K-D-G-R-F-A-I-K (SEQ ID NO: 5); L-K-K-D-D-N-I-A-A-A-L-V-L-R-G-I-A-K-D-G-R-F-A-I-K (SEQ ID NO: 6); L-K-K-D-D-N-I-A-A-A-V-V-L-R-G-L-V-K-D-G-R-F-A-I-K (SEQ ID NO: 7); L-K-K-D-D-N-I-A-A-A-L-V-L-R-G-L-V-K-D-G-R-F-A-I-K (SEQ ID NO: 8); L-K-K-D-D-N-I-A-A-A-V-V-L-R-G-I-V-K-D-G-R-F-A-I-K (SEQ ID NO: 9); L-K-K-D-D-N-I-A-A-A-L-V-L-R-G-I-V-K-D-G-R-F-A-I-K (SEQ ID NO: 10); L-K-K-D-D-N-I-A-A-A-V-V-L-R-G-L-A-K-D-G-D-F-A-I-K (SEQ ID NO: 11); L-K-K-D-D-N-I-A-A-A-L-V-L-R-G-L-A-K-D-G-D-F-A-I-K (SEQ ID NO: 12); L-K-K-D-D-N-I-A-A-A-V-V-L-R-G-I-A-K-D-G-D-F-A-I-K (SEQ ID NO: 13); L-K-K-D-D-N-I-A-A-A-L-V-L-R-G-I-A-K-D-G-D-F-A-I-K (SEQ ID NO: 14); L-K-K-D-D-N-I-A-A-A-V-V-L-R-G-L-V-K-D-G-D-F-A-I-K (SEQ ID NO: 15); L-K-K-D-D-N-I-A-A-A-L-V-L-R-G-L-V-K-D-G-D-F-A-I-K (SEQ ID NO: 16); L-K-K-D-D-N-I-A-A-A-V-V-L-R-G-I-V-K-D-G-D-F-A-I-K (SEQ ID NO: 17); L-K-K-D-D-N-I-A-A-A-L-V-L-R-G-I-V-K-D-G-D-F-A-I-K (SEQ ID NO: 18); L-K-K-D-D-N-I-A-A-A-V-V-L-R-G-L-A-K-D-G-N-F-A-I-K (SEQ ID NO: 19); L-K-K-D-D-N-I-A-A-A-L-V-L-R-G-L-A-K-D-G-N-F-A-I-K (SEQ ID NO: 20); L-K-K-D-D-N-I-A-A-A-V-V-L-R-G-I-A-K-D-G-N-F-A-I-K (SEQ ID NO: 21); L-K-K-D-D-N-I-A-A-A-L-V-L-R-G-I-A-K-D-G-N-F-A-I-K (SEQ ID NO: 22); L-K-K-D-D-N-I-A-A-A-V-V-L-R-G-L-V-K-D-G-N-F-A-I-K (SEQ ID NO: 23); L-K-K-D-D-N-I-A-A-A-L-V-L-R-G-L-V-K-D-G-N-F-A-I-K (SEQ ID NO: 24); L-K-K-D-D-N-I-A-A-A-V-V-L-R-G-I-V-K-D-G-N-F-A-I-K (SEQ ID NO:

25); L-K-K-D-D-N-I-A-A-A-L-V-L-R-G-I-V-K-D-G-N-F-A-I-K (SEQ ID NO: 26); L-K-K-D-D-N-I-A-A-A-V-V-L-R-G-L-A-K-D-G-R-F-A-W-K (SEQ ID NO: 27); L-K-K-D-D-N-I-A-A-A-L-V-L-R-G-L-A-K-D-G-R-F-A-W-K (SEQ ID NO: 28); L-K-K-D-D-N-I-A-A-A-V-V-L-R-G-I-A-K-D-G-R-F-A-W-K (SEQ ID NO: 29); L-K-K-D-D-N-I-A-A-A-L-V-L-R-G-I-A-K-D-G-R-F-A-W-K (SEQ ID NO: 30); L-K-K-D-D-N-I-A-A-A-V-V-L-R-G-L-V-K-D-G-R-F-A-W-K (SEQ ID NO: 31); L-K-K-D-D-N-I-A-A-A-L-V-L-R-G-L-V-K-D-G-R-F-A-W-K (SEQ ID NO: 32); L-K-K-D-D-N-I-A-A-A-V-V-L-R-G-I-V-K-D-G-R-F-A-W-K (SEQ ID NO: 33); L-K-K-D-D-N-I-A-A-A-L-V-L-R-G-I-V-K-D-G-R-F-A-W-K (SEQ ID NO: 34); L-K-K-D-D-N-I-A-A-A-V-V-L-R-G-L-A-K-D-G-D-F-A-W-K (SEQ ID NO: 35); L-K-K-D-D-N-I-A-A-A-L-V-L-R-G-L-A-K-D-G-D-F-A-W-K (SEQ ID NO: 36); L-K-K-D-D-N-I-A-A-A-V-V-L-R-G-I-A-K-D-G-D-F-A-W-K (SEQ ID NO: 37); L-K-K-D-D-N-I-A-A-A-L-V-L-R-G-I-A-K-D-G-D-F-A-W-K (SEQ ID NO: 38); L-K-K-D-D-N-I-A-A-A-V-V-L-R-G-L-V-K-D-G-D-F-A-W-K (SEQ ID NO: 39); L-K-K-D-D-N-I-A-A-A-L-V-L-R-G-L-V-K-D-G-D-F-A-W-K (SEQ ID NO: 40); L-K-K-D-D-N-I-A-A-A-V-V-L-R-G-I-V-K-D-G-D-F-A-W-K (SEQ ID NO: 41); L-K-K-D-D-N-I-A-A-A-L-V-L-R-G-I-V-K-D-G-D-F-A-W-K (SEQ ID NO: 42); L-K-K-D-D-N-I-A-A-A-V-V-L-R-G-L-A-K-D-G-N-F-A-W-K (SEQ ID NO: 43); L-K-K-D-D-N-I-A-A-A-L-V-L-R-G-L-A-K-D-G-N-F-A-W-K (SEQ ID NO: 44); L-K-K-D-D-N-I-A-A-A-V-V-L-R-G-I-A-K-D-G-N-F-A-W-K (SEQ ID NO: 45); L-K-K-D-D-N-I-A-A-A-L-V-L-R-G-I-A-K-D-G-N-F-A-W-K (SEQ ID NO: 46); L-K-K-D-D-N-I-A-A-A-V-V-L-R-G-L-V-K-D-G-N-F-A-W-K (SEQ ID NO: 47); L-K-K-D-D-N-I-A-A-A-L-V-L-R-G-L-V-K-D-G-N-F-A-W-K (SEQ ID NO: 48); L-K-K-D-D-N-I-A-A-A-V-V-L-R-G-I-V-K-D-G-N-F-A-W-K (SEQ ID NO: 49); L-K-K-D-D-N-I-A-A-A-L-V-L-R-G-I-V-K-D-G-N-F-A-W-K (SEQ ID NO: 50); L-K-K-D-D-N-I-A-A-A-V-V-L-R-G-L-A-K-D-G-R-F-A-Y-K (SEQ ID NO: 51); L-K-K-D-D-N-I-A-A-A-L-V-L-R-G-L-A-K-D-G-R-F-A-Y-K (SEQ ID NO: 52); L-K-K-D-D-N-I-A-A-A-V-V-L-R-G-I-A-K-D-G-R-F-A-Y-K (SEQ ID NO: 53); L-K-K-D-D-N-I-A-A-A-L-V-L-R-G-I-A-K-D-G-R-F-A-Y-K (SEQ ID NO: 54); L-K-K-D-D-N-I-A-A-A-V-V-L-R-G-L-V-K-D-G-R-F-A-Y-K (SEQ ID NO: 55); L-K-K-D-D-N-I-A-A-A-L-V-L-R-G-L-V-K-D-G-R-F-A-Y-K (SEQ ID NO: 56); L-K-K-D-D-N-I-A-A-A-V-V-L-R-G-I-V-K-D-G-R-F-A-Y-K (SEQ ID NO: 57); L-K-K-D-D-N-I-A-A-A-L-V-L-R-G-I-V-K-D-G-R-F-A-Y-K (SEQ ID NO: 58); L-K-K-D-D-N-I-A-A-A-V-V-L-R-G-L-A-K-D-G-D-F-A-Y-K (SEQ ID NO: 59); L-K-K-D-D-N-I-A-A-A-L-V-L-R-G-L-A-K-D-G-D-F-A-Y-K (SEQ ID NO: 60); L-K-K-D-D-N-I-A-A-A-V-V-L-R-G-I-A-K-D-G-D-F-A-Y-K (SEQ ID NO: 61); L-K-K-D-D-N-I-A-A-A-L-V-L-R-G-I-A-K-D-G-D-F-A-Y-K (SEQ ID NO: 62); L-K-K-D-D-N-I-A-A-A-V-V-L-R-G-L-V-K-D-G-D-F-A-Y-K (SEQ ID NO: 63); L-K-K-D-D-N-I-A-A-A-L-V-L-R-G-L-V-K-D-G-D-F-A-Y-K (SEQ ID NO: 64); L-K-K-D-D-N-I-A-A-A-V-V-L-R-G-I-V-K-D-G-D-F-A-Y-K (SEQ ID NO: 65); L-K-K-D-D-N-I-A-A-A-L-V-L-R-G-I-V-K-D-G-D-F-A-Y-K (SEQ ID NO: 66); L-K-K-D-D-N-I-A-A-A-V-V-L-R-G-L-A-K-D-G-N-F-A-Y-K (SEQ ID NO: 67); L-K-K-D-D-N-I-A-A-A-L-V-L-R-G-L-A-K-D-G-N-F-A-Y-K (SEQ ID NO: 68); L-K-K-D-D-N-I-A-A-A-V-V-L-R-G-I-A-K-D-G-N-F-A-Y-K (SEQ ID NO: 69); L-K-K-D-D-N-I-A-A-A-L-V-L-R-G-I-A-K-D-G-N-F-A-Y-K (SEQ ID NO: 70); L-K-K-D-D-N-I-A-A-A-V-V-L-R-G-L-V-K-D-G-N-F-A-Y-K (SEQ ID NO: 71); L-K-K-D-D-N-I-A-A-A-L-V-L-R-G-L-V-K-D-G-N-F-A-Y-K (SEQ ID NO: 72); L-K-K-D-D-N-I-A-A-A-V-V-L-R-G-I-V-K-D-G-N-F-A-Y-K (SEQ ID NO: 73); L-K-K-D-D-N-I-A-A-A-L-V-L-R-G-I-V-K-D-G-N-F-A-Y-K (SEQ ID NO: 74); L-K-K-D-D-N-I-A-A-A-V-V-L-R-G-L-A-K-D-G-R-F-A-I-R (SEQ ID NO: 75); L-K-K-D-D-N-I-A-A-A-L-V-L-R-G-L-A-K-D-G-R-F-A-I-R (SEQ ID NO: 76); L-K-K-D-D-N-I-A-A-A-V-V-L-R-G-I-A-K-D-G-R-F-A-I-R (SEQ ID NO: 77); L-K-K-D-D-N-I-A-A-A-L-V-L-R-G-I-A-K-D-G-R-F-A-I-R (SEQ ID NO: 78); L-K-K-D-D-N-I-A-A-A-V-V-L-R-G-L-V-K-D-G-R-F-A-I-R (SEQ ID NO: 79); L-K-K-D-D-N-I-A-A-A-L-V-L-R-G-L-V-K-D-G-R-F-A-I-R (SEQ ID NO: 80); L-K-K-D-D-N-I-A-A-A-V-V-L-R-G-I-V-K-D-G-R-F-A-I-R (SEQ ID NO: 81); L-K-K-D-D-N-I-A-A-A-L-V-L-R-G-I-V-K-D-G-R-F-A-I-R (SEQ ID NO: 82); L-K-K-D-D-N-I-A-A-A-V-V-L-R-G-L-A-K-D-G-D-F-A-I-R (SEQ ID NO: 83); L-K-K-D-D-N-I-A-A-A-L-V-L-R-G-L-A-K-D-G-D-F-A-I-R (SEQ ID NO: 84); L-K-K-D-D-N-I-A-A-A-V-V-L-R-G-I-A-K-D-G-D-F-A-I-R (SEQ ID NO: 85); L-K-K-D-D-N-I-A-A-A-L-V-L-R-G-I-A-K-D-G-D-F-A-I-R (SEQ ID NO: 86); L-K-K-D-D-N-I-A-A-A-V-V-L-R-G-L-V-K-D-G-D-F-A-I-R (SEQ ID NO: 87); L-K-K-D-D-N-I-A-A-A-L-V-L-R-G-L-V-K-D-G-D-F-A-I-R (SEQ ID NO: 88); L-K-K-D-D-N-I-A-A-A-V-V-L-R-G-I-V-K-D-G-D-F-A-I-R (SEQ ID NO: 89); L-K-K-D-D-N-I-A-A-A-L-V-L-R-G-I-V-K-D-G-D-F-A-I-R (SEQ ID NO: 90); L-K-K-D-D-N-I-A-A-A-V-V-L-R-G-L-A-K-D-G-N-F-A-I-R (SEQ ID NO: 91); L-K-K-D-D-N-I-A-A-A-L-V-L-R-G-L-A-K-D-G-N-F-A-I-R (SEQ ID NO: 92); L-K-K-D-D-N-I-A-A-A-V-V-L-R-G-I-A-K-D-G-N-F-A-I-R (SEQ ID NO: 93); L-K-K-D-D-N-I-A-A-A-L-V-L-R-G-I-A-K-D-G-N-F-A-I-R (SEQ ID NO: 94); L-K-K-D-D-N-I-A-A-A-V-V-L-R-G-L-V-K-D-G-N-F-A-I-R (SEQ ID NO: 95); L-K-K-D-D-N-I-A-A-A-L-V-L-R-G-L-V-K-D-G-N-F-A-I-R (SEQ ID NO: 96); L-K-K-D-D-N-I-A-A-A-V-V-L-R-G-I-V-K-D-G-N-F-A-I-R (SEQ ID NO: 97); L-K-K-D-D-N-I-A-A-A-L-V-L-R-G-I-V-K-D-G-N-F-A-I-R (SEQ ID NO: 98); L-K-K-D-D-N-I-A-A-A-V-V-L-R-G-L-A-K-D-G-R-F-A-W-R (SEQ ID NO: 99); L-K-K-D-D-N-I-A-A-A-L-V-L-R-G-L-A-K-D-G-R-F-A-W-R (SEQ ID NO: 100); L-K-K-D-D-N-I-A-A-A-V-V-L-R-G-I-A-K-D-G-R-F-A-W-R (SEQ ID NO: 101); L-K-K-D-D-N-I-A-A-A-L-V-L-R-G-I-A-K-D-G-R-F-A-W-R (SEQ ID NO: 102); L-K-K-D-D-N-I-A-A-A-V-V-L-R-G-L-V-K-D-G-R-F-A-W-R (SEQ ID NO: 103); L-K-K-D-D-N-I-A-A-A-L-V-L-R-G-L-V-K-D-G-R-F-A-W-R (SEQ ID NO: 104); L-K-K-D-D-N-I-A-A-A-V-V-L-R-G-I-V-K-D-G-R-F-A-W-R (SEQ ID NO: 105); L-K-K-D-D-N-I-A-A-A-L-V-L-R-G-I-V-K-D-G-R-F-A-W-R (SEQ ID NO: 106); L-K-K-D-D-N-I-A-A-A-V-V-L-R-G-L-A-K-D-G-D-F-A-W-R (SEQ ID NO: 107); L-K-K-D-D-N-I-A-A-A-L-V-L-R-G-L-A-K-D-G-D-F-A-W-R (SEQ ID NO: 108); L-K-K-D-D-N-I-A-A-A-V-V-L-R-G-I-A-K-D-G-D-F-A-W-R (SEQ ID NO: 109); L-K-K-D-D-N-I-A-A-A-L-V-L-R-G-I-A-K-D-G-D-F-A-W-R (SEQ ID NO: 110); L-K-K-D-D-N-I-A-A-A-V-V-L-R-G-L-V-K-D-G-D-F-A-W-R (SEQ ID NO: 111); L-K-K-D-D-N-I-A-A-A-L-V-L-R-G-L-V-K-D-G-D-F-A-W-R (SEQ ID NO: 112); L-K-K-D-D-N-I-A-A-A-V-V-L-R-G-I-V-K-D-G-D-F-A-W-R (SEQ ID NO: 113); L-K-K-D-D-N-I-A-A-A-L-V-L-R-G-I-V-K-D-G-D-F-A-W-R (SEQ ID NO: 114); L-K-K-D-D-N-I-A-A-A-V-V-L-R-G-L-A-K-D-G-N-F-A-W-R (SEQ ID NO: 115); L-K-K-D-D-N-I-A-A-A-L-V-L-R-G-L-A-K-D-G-N-F-A-W-R (SEQ ID NO: 116); L-K-K-D-D-N-I-A-A-A-V-V-L-R-G-I-A-K-D-G-N-F-A-W-R (SEQ ID NO: 117); L-K-K-D-D-N-I-A-A-A-L-V-L-R-G-I-A-K-D-G-N-F-A-W-R (SEQ ID NO: 118); L-K-K-D-D-N-I-A-A-A-V-V-L-R-G-L-V-K-D-G-N-F-A-W-R (SEQ ID NO: 119); L-K-K-D-D-N-I-A-A-A-L-V-L-R-G-L-V-K-D-G-N-F-A-W-R (SEQ ID NO: 120); L-K-K-D-D-N-I-A-A-A-V-V-L-R-G-I-V-K-D-G-N-F-A-W-R (SEQ ID NO: 121); L-K-K-D-D-N-I-A-A-A-

L-V-L-R-G-I-V-K-D-G-N-F-A-W-R (SEQ ID NO: 122); L-K-K-D-D-N-I-A-A-A-V-V-L-R-G-L-A-K-D-G-R-F-A-Y-R (SEQ ID NO: 123); L-K-K-D-D-N-I-A-A-A-L-V-L-R-G-L-A-K-D-G-R-F-A-Y-R (SEQ ID NO: 124); L-K-K-D-D-N-I-A-A-A-V-V-L-R-G-I-A-K-D-G-R-F-A-Y-R (SEQ ID NO: 125); L-K-K-D-D-N-I-A-A-A-L-V-L-R-G-I-A-K-D-G-R-F-A-Y-R (SEQ ID NO: 126); L-K-K-D-D-N-I-A-A-A-V-V-L-R-G-L-V-K-D-G-R-F-A-Y-R (SEQ ID NO: 127); L-K-K-D-D-N-I-A-A-A-L-V-L-R-G-L-V-K-D-G-R-F-A-Y-R (SEQ ID NO: 128); L-K-K-D-D-N-I-A-A-A-V-V-L-R-G-I-V-K-D-G-R-F-A-Y-R (SEQ ID NO: 129); L-K-K-D-D-N-I-A-A-A-L-V-L-R-G-I-V-K-D-G-R-F-A-Y-R (SEQ ID NO: 130); L-K-K-D-D-N-I-A-A-A-V-V-L-R-G-L-A-K-D-G-D-F-A-Y-R (SEQ ID NO: 131); L-K-K-D-D-N-I-A-A-A-L-V-L-R-G-L-A-K-D-G-D-F-A-Y-R (SEQ ID NO: 132); L-K-K-D-D-N-I-A-A-A-V-V-L-R-G-I-A-K-D-G-D-F-A-Y-R (SEQ ID NO: 133); L-K-K-D-D-N-I-A-A-A-L-V-L-R-G-I-A-K-D-G-D-F-A-Y-R (SEQ ID NO: 134); L-K-K-D-D-N-I-A-A-A-V-V-L-R-G-L-V-K-D-G-D-F-A-Y-R (SEQ ID NO: 135); L-K-K-D-D-N-I-A-A-A-L-V-L-R-G-L-V-K-D-G-D-F-A-Y-R (SEQ ID NO: 136); L-K-K-D-D-N-I-A-A-A-V-V-L-R-G-I-V-K-D-G-D-F-A-Y-R (SEQ ID NO: 137); L-K-K-D-D-N-I-A-A-A-L-V-L-R-G-I-V-K-D-G-D-F-A-Y-R (SEQ ID NO: 138); L-K-K-D-D-N-I-A-A-A-V-V-L-R-G-L-A-K-D-G-N-F-A-Y-R (SEQ ID NO: 139); L-K-K-D-D-N-I-A-A-A-L-V-L-R-G-L-A-K-D-G-N-F-A-Y-R (SEQ ID NO: 140); L-K-K-D-D-N-I-A-A-A-V-V-L-R-G-I-A-K-D-G-N-F-A-Y-R (SEQ ID NO: 141); L-K-K-D-D-N-I-A-A-A-L-V-L-R-G-I-A-K-D-G-N-F-A-Y-R (SEQ ID NO: 142); L-K-K-D-D-N-I-A-A-A-V-V-L-R-G-L-V-K-D-G-N-F-A-Y-R (SEQ ID NO: 143); L-K-K-D-D-N-I-A-A-A-L-V-L-R-G-L-V-K-D-G-N-F-A-Y-R (SEQ ID NO: 144); L-K-K-D-D-N-I-A-A-A-V-V-L-R-G-I-V-K-D-G-N-F-A-Y-R (SEQ ID NO: 145); or L-K-K-D-D-N-I-A-A-A-L-V-L-R-G-I-V-K-D-G-N-F-A-Y-R (SEQ ID NO: 146).

In certain embodiments, peptides of the invention comprise a sequence of SEQ ID NO: 1 and an additional N-terminal peptide sequence (e.g., an N-terminal extension). The additional N-terminal peptide sequence can comprise 1, 2, 3, 4, 5, 6, 7, 8, 9, 10, 11, 12, 13, 14, 15, 20, 25, or more amino acids. In certain embodiments, the N-terminal peptide sequence has a length of about 5 to about 10, about 10 to about 15, about 15 to about 20, about 20 to about 25, about 25 to about 30, about 30 to about 40, or about 40 to about 50 amino acids. The additional N-terminal peptide sequence can be a native sequence. As used herein, a "native" sequence is a peptide sequence from a naturally-occurring *Borrelia* VlsE sequence, or a variant thereof. In certain embodiments, the peptide sequence is a fragment of a naturally-occurring *Borrelia* VlsE sequence. The peptide sequence can be, e.g., from a conserved or non-conserved region of VlsE. The peptide sequence can comprise, e.g., an epitope, such as an immunodominant epitope or any other epitope recognizable by a host (e.g., human, dog, etc.) immune system. VlsE proteins and peptides thereof have been described, e.g., in U.S. Pat. Nos. 6,475,492, 6,660,274, 6,719,983, 6,740,744, and 7,887,815, and European Patent Nos. 0894143, 1012181, 1171605, and 1589109, the contents of which are incorporated herein by reference.

Variant polypeptides are at least about 80, 85, 90, 95, 98, or 99% identical to a peptide shown in SEQ ID NOs: 1-146 and are also polypeptides of the invention. Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants of the peptide sequences can be readily selected by one of skill in the art, based in part on known properties of the sequence. For example, a variant peptide can include amino acid substitutions (e.g., conservative amino acid substitutions) and/or deletions (e.g., small, single amino acid deletions, or deletions encompassing 2, 3, 4, 5, 10, 15, 20, or more contiguous amino acids). Thus, in certain embodiments, a variant of a native peptide sequence is one that differs from a naturally-occurring sequence by (i) one or more (e.g., 2, 3, 4, 5, 6, or more) conservative amino acid substitutions, (ii) deletion of 1 or more (e.g., 2, 3, 4, 5, 6, or more) amino acids, or (iii) a combination thereof. Deleted amino acids can be contiguous or non-contiguous. Conservative amino acid substitutions are those that take place within a family of amino acids that are related in their side chains and chemical properties. These include, e.g., (1) acidic amino acids: aspartate, glutamate; (2) basic amino acids: lysine, arginine, histidine; (3) nonpolar amino acids: alanine, valine, leucine, isoleucine, proline, phenylalanine, methionine, tryptophan; (4) uncharged polar amino acids: glycine, asparagine, glutamine, cysteine, serine, threonine, tyrosine; (5) aliphatic amino acids: glycine, alanine, valine, leucine, isoleucine, serine, threonine, with serine and threonine optionally grouped separately as aliphatic-hydroxyl; (6) aromatic amino acids: phenylalanine, tyrosine, tryptophan; (7) amide amino acids: asparagine, glutamine; and (9) sulfur-containing amino acids: cysteine and methionine. See, e.g., Biochemistry, 2nd ed., Ed. by L. Stryer, W H Freeman and Co.: 1981. Methods for confirming that variant peptides are suitable are conventional and routine.

Variants of the peptide sequences encompass variations on previously defined peptide sequences. For example, a previously described peptide sequence comprising a known epitope may be lengthened or shortened, at one or both ends (e.g., by about 1-3 amino acids), and/or one, two, three, four or more amino acids may be substituted by conservative amino acids, etc. Furthermore, if a region of a protein has been identified as containing an epitope of interest, an investigator can "shift" the region of interest (e.g., by about 5 amino acids in either direction) from the endpoints of the original rough region to optimize the activity.

In certain embodiments, the additional N-terminal peptide sequence can comprise or consist of another IR6 domain peptide. In other embodiments, the native sequence is a VlsE sequence that is naturally adjacent to the N-terminal end of a VlsE IR6 domain.

In certain embodiments, the additional N-terminal peptide sequence is a non-native sequence. As used herein, a "non-native" sequence is any protein sequence, whether from a *Borrelia* protein or otherwise, other than a native VlsE peptide sequence. In certain embodiments, the additional N-terminal peptide sequence comprises an epitope of a *Borrelia* antigen, such as OspA, OspB, DbpA, flagella-associated proteins FlaA (p37) and FlaB (p41), OspC (25 kd), BBK32, BmpA (p39), p21, p39, p66 or p83. Polypeptides or peptides derived from other microorganisms can also be used.

A peptide of the invention comprising an additional N-terminal peptide sequence can be designed for diagnosing *Borrelia* infections early after infection (e.g., within one to two weeks after the onset of infection). Among the pathogenic *Borrelia* proteins whose expression has been recognized in early stages of infection (e.g., to which IgM antibody appears early after infection) are OspC, BBK32, the flagella-associated protein FlaB (p41), and, to a lesser extent, BmpA (p39), and the flagella-associated protein FlaA (p37). Polypeptides or peptides which derive from those polypeptides are suitable for assays for early infection. For example, some suitable linear epitopes which can be used for the diagnosis of early infection include peptides in OspC: PVVAESPKKP (SEQ ID NO: 147), ILMTLFLFISCNNS (SEQ ID NO: 148), and one or more epitopes contained between amino acids 161 and 210, as reported by Jobe et al. (2003) Clin Diagn Lab Immunol 10, 573-8), the contents of which are incorporated herein by reference. The OspC peptides described in U.S. Pat. No. 6,716,574, the contents of which are incorporated herein by reference, can also be used. Other suitable regions, which have been shown not to contain major cross-reactive epitopes, have been identified in FlaB (p41), such as residues 120 to 235. See, e.g., Crother et al. ((2003) Infect. Immun. 71, 3419-3428; Wang et al. (1999)) Clin Microbial Rev 12, 633-653; and U.S. Pat. Nos. 5,618,533, 5,643,733, 5,643,751, 5,932,220, and 6,617,441, the contents of each of which is incorporated herein by reference. Other peptides bearing either linear or conformational epitopes are known in the art. Methods for identifying additional non-native epitope sequences, particularly from variable regions of, e.g., OspC, BBK32 or DbpA, are discussed in, e.g., U.S. Pat. No. 7,887,815.

In certain embodiments, the additional N-terminal peptide sequence is from OspC. For example, in certain embodiments, the additional N-terminal peptide sequence is a sequence of SEQ ID NO: 149, $n_1$-$n_2$-S-P-$n_5$-$n_6$-P (SEQ ID NO: 149) or a fragment thereof (e.g., a C-terminal fragment), wherein $n_1$ is an amino acid selected from the group consisting of A and V, $n_2$ is an amino acid selected from the group consisting of E and D, $n_5$ is an amino acid selected from the group consisting of K and R, and $n_6$ is an amino acid selected from the group consisting of K and R.

In certain embodiments, the additional N-terminal peptide sequence is a combination of sequences. For example, the additional N-terminal peptide sequence can comprise a native, a non-native sequence, or any combination of such sequences (e.g., two or more native sequences, two or more non-native sequence, a native and non-native sequence, etc.).

In certain embodiments, peptides of the invention comprise a sequence defined by SEQ ID NO: 1 and further comprise an additional C-terminal sequence. The additional C-terminal peptide sequence can comprise 1, 2, 3, 4, 5, 6, 7, 8, 9, 10, 11, 12, 13, 14, 15, 20, 25, or more amino acids. The additional C-terminal peptide sequence can be a native sequence. For example, in certain embodiments, the additional C-terminal peptide sequence can comprise or consist of another IR6 domain peptide. In other embodiments, the native sequence is a VlsE sequence that is naturally adjacent to the C-terminal end of a VlsE IR6 domain.

In certain embodiments, the additional C-terminal peptide sequence is a non-native sequence. In certain embodiments, the additional C-terminal peptide sequence comprises an epitope of a *Borrelia* antigen, such as OspA, OspB, DbpA, flagella-associated proteins FlaA (p37) and FlaB (p41), OspC (25 kd), BBK32, BmpA (p39), p21, p39, p66 or p83, as discussed above. Polypeptides or peptides derived from other microorganisms can also be used.

In certain embodiments, the additional C-terminal peptide sequence is from FlaB (p41). For example, in certain embodiments, the additional C-terminal peptide sequence is a sequence of SEQ ID NO: 150, V-$c_2$-E-G-$c_5$-Q-Q-E-G-A-Q-Q-P-S-C (SEQ ID NO: 150) or a fragment thereof (e.g., an N-terminal fragment), wherein $c_2$ is an amino acid selected from the group consisting of Q and R, and $c_5$ is an amino acid selected from the group consisting of V and A. In other embodiments, the additional C-terminal peptide sequence is a sequence of SEQ ID NO: 151, A-V-$c_3$-E-G-$c_6$-Q-Q-E-G-A-Q-Q-P-S-C (SEQ ID NO: 151) or a fragment thereof (e.g., an N-terminal fragment), wherein $c_3$ is an amino acid selected from the group consisting of Q and R, and $c_6$ is an amino acid selected from the group consisting of V and A.

In certain embodiments, the additional C-terminal peptide sequence is a combination of sequences. For example, the additional C-terminal peptide sequence can comprise a native, a non-native sequence, or any combination of such sequences (e.g., two or more native sequences, two or more non-native sequence, a native and non-native sequence, etc.).

In certain embodiments, peptides of the invention comprise a sequence defined by SEQ ID NO: 1 and further comprise an additional N-terminal peptide sequence and an additional C-terminal peptide sequence. The additional N-terminal and C-terminal peptide sequences can be as described above. Peptides of the invention do not consist of a full-length VlsE protein. However, in certain embodiments, peptides of the invention can comprise a full-length VlsE protein. In other embodiments, peptides of the invention do not comprise a full-length VlsE protein.

In addition to the sequences described above, the additional N-terminal and C-terminal sequences can comprise or consist of a flexible sequence, designed to better present the peptides of the invention for detection in an immunoassay (e.g., ELISA assay, lateral flow immunoassay, agglutination assay, etc.). Such flexible sequences can be readily identified by persons skilled in the art.

In certain embodiments, the peptides of the invention comprise or consist of a sequence of SEQ ID NO: 2, $n_1$-$n_2$-S-P-$n_5$-$n_6$-P-L-K-K-D-D-N-I-A-A-A-$X_{18}$-V-L-R-G-$X_{23}$-$X_{24}$-K-D-G-$X_{28}$-F-A-$X_{31}$-$X_{32}$-A-V-$c_{35}$-E-G-$c_{38}$-Q-Q-E-G-A-Q-Q-P-S-C (SEQ ID NO: 2) wherein $n_1$ is an amino acid selected from the group consisting of A and V, $n_2$ is an amino acid selected from the group consisting of E and D, $n_5$ is an amino acid selected from the group consisting of K and R, $n_6$ is an amino acid selected from the group consisting of K and R, $X_{18}$ is an amino acid selected from the group consisting of V and L, $X_{23}$ is an amino acid selected from the group consisting of L and I, $X_{24}$ is an amino acid selected from the group consisting of A and V, $X_{28}$ is an amino acid selected from the group consisting of R, D and N, $X_{31}$ is an amino acid selected from the group consisting of I, W, and Y, $X_{32}$ is an amino acid selected from the group consisting of K, and R, $c_{35}$ is an amino acid selected from the group consisting of Q and R, and $c_{38}$ is an amino acid selected from the group consisting of V and A.

In certain embodiments, peptides of the invention comprise a sequence defined by SEQ ID NO: 2 and further comprise an additional N-terminal peptide sequence, an additional C-terminal peptide sequence, or a combination thereof. The additional N-terminal and C-terminal peptide sequences can be as described above.

In certain embodiments, peptides of the invention comprise or consist of 25 or more (e.g., 26, 27, 28, 29, or more) amino acid residues. In certain embodiments, peptides of the invention comprise or consist of 30 or more (e.g., 31, 32, 33, 34, or more) amino acid residues. In certain embodiments, peptides of the invention comprise or consist of 35 or more (e.g., 36, 37, 38, 39, or more) amino acid residues. In certain embodiments, peptides of the invention comprise or consist of 40 or more (e.g., 41, 42, 43, 44, or more) amino acid residues. In certain embodiments, peptides of the invention comprise or consist of 45 or more (e.g., 46, 47, 48, 49, or more) amino acid residues. In certain embodiments, peptides of the invention comprise or consist of 50 or more (e.g., 51, 52, 53, 54, or more) amino acid residues. In certain embodiments, peptides of the invention comprise or consist of 55, 60, 65, 70, 75, 80, 85, 90, 95, 100, or more amino acid residues.

In certain embodiments, peptides of the invention comprise an epitope of a peptide sequence described herein. For example, in certain embodiments, peptides of the invention comprise an epitope of a sequence selected from the group consisting of SEQ ID NO: 1-146.

In certain embodiments, peptides of the invention comprise a fragment of a peptide sequence described herein. For example, in certain embodiments, peptides of the invention comprise a fragment of a sequence selected from the group consisting of SEQ ID NO: 1-146. The fragment can be, e.g., at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids in length. The fragment can be contiguous or can include one or more deletions (e.g., a deletion of 1, 2, 3, 4, 5, 6, 7, 8, 9, 10, or more amino acid residues). In certain embodiments, the fragment comprises a sequence set forth in U.S. Pat. Nos. 6,475,492, 6,660,274, 6,719,983, 6,740,744, or 7,887,815, or European Patent Nos. 0894143, 1012181, 1171605, or 1589109. In certain embodiments, the fragment does not consist of a sequence set forth in one or more of U.S. Pat. Nos. 6,475,492, 6,660,274, 6,719,983, 6,740,744, and 7,887,815, and European Patent Nos. 0894143, 1012181, 1171605, and 1589109. Peptides of the invention that comprise a fragment of a peptide sequence described herein can further comprise an additional N-terminal peptide sequence, an additional C-terminal peptide sequence, or a combination thereof. The additional N-terminal and C-terminal peptide sequences can be as described above.

Peptides of the invention comprising an additional N-terminal or C-terminal peptide sequence can further comprise a linker connecting the peptide (e.g., a peptide of SEQ ID NO: 1 or SEQ ID NO: 2, or a fragment thereof) with the additional N-terminal or C-terminal peptide sequence. The linker can be, e.g., a peptide spacer. Such a spacer can consist of, for example, between about one and five (e.g., about three) amino acid residues, preferably uncharged amino acids, e.g., aliphatic residues such as glycine or alanine. In one embodiment, the spacer is a triplet glycine spacer. In another embodiment, the spacer is a triplet alanine spacer. In yet another embodiment, the spacer comprises both glycine and alanine residues. Alternatively, the linker can be a chemical (i.e., non-peptide) linker.

In certain embodiments, peptides of the invention are produced by synthetic chemistry (i.e., a "synthetic peptide"). In other embodiments, peptides of the invention are produced biologically (i.e., by cellular machinery, such as a ribosome). In certain embodiments, peptides of the invention are isolated. As used herein, an "isolated" peptide is a peptide that has been produced either synthetically or biologically and then purified, at least partially, from the chemicals and/or cellular machinery used to produce the peptide. In certain embodiments, an isolated peptide of the invention is substantially purified. The term "substantially purified," as used herein, refers to a molecule, such as a peptide, that is substantially free of cellular material (proteins, lipids, carbohydrates, nucleic acids, etc.), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest. An isolated peptide of the invention can be in water, a buffer, or in a dry form awaiting reconstitution, e.g., as part of a kit. An isolated peptide of the present invention can be in the form of a pharmaceutically acceptable salt. Suitable acids and bases that are capable of forming salts with the peptides of the present invention are well known to those of skill in the art, and include inorganic and organic acids and bases.

In certain embodiments, peptides of the invention are affinity purified. For example, in certain embodiments, the peptides of the invention are purified by means of their ability to bind to anti-*Borrelia* antibodies (e.g., antibodies to VlsE proteins and, optionally, other *Borrelia* antigens) by contacting such antibodies with the peptides of the invention such that peptide-antibody complexes are able to form, washing the peptide-antibody complexes to remove impurities, and then eluting the peptides from the antibodies. The antibodies can be, e.g., attached to a solid support. Methods of affinity purification are well-known and routine to those skilled in the art.

In certain embodiments, peptides of the invention are modified. The peptides of the invention may be modified by a variety of techniques, such as by denaturation with heat and/or a detergent (e.g., SDS). Alternatively, peptides of the invention may be modified by association with one or more further moieties. The association can be covalent or non-covalent, and can be, for example, via a terminal amino acid linker, such as lysine or cysteine, a chemical coupling agent, or a peptide bond. The additional moiety can be, for example, a ligand, a ligand receptor, a fusion partner, a detectable label, an enzyme, or a substrate that immobilizes the peptide.

Peptides of the invention can be conjugated to a ligand, such as biotin (e.g., via a cysteine or lysine residue), a lipid molecule (e.g., via a cysteine residue), or a carrier protein (e.g., serum albumin, keyhole limpet hemocyanin (KLH), immunoglobulin Fc domain via e.g., a cysteine or lysine residue). Attachment to ligands, such as biotin, can be useful for associating the peptide with ligand receptors, such as avidin, streptavidin, polymeric streptavidin (see e.g., US 2010/0081125 and US 2010/0267166, both of which are herein incorporated by reference), or neutravidin. Avidin, streptavidin, polymeric streptavidin, neutravidin, in turn, can be linked to a signaling moiety (e.g., a moiety that can be visualized, such as colloidal gold, a fluorescent moiety, or an enzyme (horseradish peroxidase or alkaline phosphatase) or a solid substrate (e.g., an Immobilon or nitrocellulose membrane). Alternatively, the peptides of the invention can be fused or linked to a ligand receptor, such as avidin, streptavidin, polymeric streptavidin, or neutravidin, thereby facilitating the association of the peptides with the corresponding ligand, such as biotin and any moiety (e.g., signaling moiety) or solid substrate attached thereto. Examples of other ligand-receptor pairs are well-known in the art and can similarly be used. In some embodiments, the peptides of the invention can be linked or conjugated to a signaling moiety directly.

Peptides of the invention can be fused or conjugated to a fusion partner (e.g., a peptide or other moiety). In some embodiments, a fusion partner can facilitate purification, expression of the peptide in a host cell, detection, stabilize the peptide, connecting the peptide to a surface or other entities, etc. Examples of suitable compounds for fusion partners include carrier proteins (e.g., serum albumin, immunoglobulin Fc domain, dendrimer, etc.), beta-galactosidase, glutathione-S-transferase, a histidine tag, etc. The fusion can be achieved by means of, e.g., a peptide bond. For example, peptides of the invention and fusion partners can be fusion proteins and can be directly fused in-frame or can comprise a peptide linker, as discussed above in the context of additional N-terminal and C-terminal peptide sequences. In certain embodiments, a mixture of peptides of the invention can be linked by a dendrimer, e.g., as in a MAPS structure.

In addition, peptides of the invention may be modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included. Peptides of the invention that consist of any of the sequences discussed herein may be modified by any of the discussed modifications. Such peptides still "consist of" the amino acids.

Modifications as set forth above are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins-Structure and Molecular Properties, 2nd ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

In certain embodiments, peptides of the invention are attached to or immobilized on a substrate, such as a solid or semi-solid support. The attachment can be covalent or non-covalent, and can be facilitated by a moiety associated with the peptide that enables covalent or non-covalent binding, such as a moiety that has a high affinity to a component attached to the carrier, support or surface. For example, the peptide can be associated with a ligand, such as biotin, and the component associated with the surface can be a corresponding ligand receptor, such as avidin. In some embodiments, the peptide can be associated with a fusion partner, e.g., bovine serum albumin (BSA), which facilitates with the attachment of the peptide to a substrate. The peptide can be attached to or immobilized on the substrate either prior to or after the addition of a sample containing antibody during an immunoassay.

In certain embodiments, the substrate is a bead, such as a colloidal particle (e.g., a colloidal nanoparticle made from gold, silver, platinum, copper, metal composites, other soft metals, core-shell structure particles, or hollow gold nanospheres) or other type of particle (e.g., a magnetic bead or a particle or nanoparticle comprising silica, latex, polystyrene, polycarbonate, polyacrylate, or PVDF). Such particles can comprise a label (e.g., a colorimetric, chemiluminescent, or fluorescent label) and can be useful for visualizing the location of the peptides during immunoassays. In certain embodiments, a terminal cysteine of a peptide of the invention is used to bind the peptide directly to the nanoparticles made from gold, silver, platinum, copper, metal composites, other soft metals, etc.

In certain embodiments, the substrate is a dot blot or a flow path in a lateral flow immunoassay device. For example, the peptides can be attached or immobilized on a porous membrane, such as a PVDF membrane (e.g., an Immobilon™ membrane), a nitrocellulose membrane, polyethylene membrane, nylon membrane, or a similar type of membrane.

In certain embodiments, the substrate is a flow path in an analytical rotor. In other embodiments, the substrate is a tube or a well, such as a well in a plate (e.g., a microtiter plate) suitable for use in an ELISA assay. Such substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A substrate can be sintered, fine particles of polyethylene, commonly known as porous polyethylene, for example, 0.2-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

Accordingly, in another aspect, the invention provides devices. In certain embodiments, the devices are useful for performing an immunoassay. For example, in certain embodiments, the device is a lateral flow immunoassay device. In other embodiments, the device is an analytical rotor. In other embodiments, the device is a dot blot, slot blot, or Western blot. In other embodiments, the device is a tube or a well, e.g., in a plate suitable for an ELISA assay. In still other embodiments, the device is an electrochemical sensor, an optical sensor, or an opto-electronic sensor.

In certain embodiments, the device comprises a peptide of the invention. In other embodiments, the device comprises a mixture of different peptides of the invention. For example, in certain embodiments, the device comprises two, three, four, or more different peptides of the invention. In certain embodiments, the peptide or each peptide in the mixture comprises a sequence of SEQ ID NO: 1 or SEQ ID NO: 2. In certain embodiments, the peptides are attached to or immobilized upon the device.

In another aspect, the invention provides compositions comprising one or more peptides of the invention. For example, in certain embodiments, the invention provides a composition comprising a peptide comprising a sequence of SEQ ID NO: 1, a peptide comprising a sequence of SEQ ID NO: 2, or mixtures thereof. In certain embodiments, the composition comprises a mixture of 2, 3, 4, 5, 6, 7, 8, 9, 10, 15, 20, 25, 30, 40, 50, 60, 70, 80, 90, 100, 150, 200, 250, 300, 400, 500, or more peptides (e.g., all possible peptides defined by SEQ ID NO: 1 or SEQ ID NO: 2). In certain embodiments, the peptides are modified (e.g., by association with one or more further moieties), as described herein.

In certain embodiments, the compositions comprise one or more peptides of the invention and one or more additional peptides, such as a *Borrelia* peptide or antigen, a peptide or antigen from one or more infectious *Borrelia* species, or a peptide or antigen from one or more causative agents of Lyme disease. The *Borrelia* peptide or antigen can be any *Borrelia* peptide or antigen described herein (e.g., an OspA, OspB, DbpA, flagella-associated proteins FlaA (p37) and FlaB (p41), OspC (25 kd), BBK32, BmpA (p39), p21, p39, p66, p83, or VlsE protein), or any fragment or epitope thereof. Some suitable *Borrelia* peptides have been described, e.g., in U.S. Pat. No. 7,887,815. The combination may comprise a cocktail (a simple mixture) of individual peptides or polypeptide, it may be in the form of a fusion peptide or polypeptide (e.g., a multimeric peptide), or the peptides may be linked by a dendrimer (e.g., as in a MAPS structure) optionally through a linking residue (e.g. lysine residue). A peptide of the invention may be fused at its N-terminus or C-terminus to another suitable peptide. Two or more copies of a peptide of the invention may be joined to one another, alone or in combination with one or more additional peptides. Combinations of fused and unfused peptides or polypeptides can be used. In one embodiment, the additional peptide(s) contain B-cell and/or T-cell epitopes from a *Borrelia* peptide or antigen, a peptide or antigen from an infectious *Borrelia* species, or a peptide or antigen from a causative agent of Lyme disease.

In another aspect, the invention provides nucleic acids comprising a sequence encoding a peptide of the invention. Nucleic acids of the invention contain less than an entire microbial genome and can be single- or double-stranded. A nucleic acid can be RNA, DNA, cDNA, genomic DNA, chemically synthesized RNA or DNA or combinations thereof. The nucleic acids can be purified free of other components, such as proteins, lipids and other polynucleotides. For example, the nucleic acids can be 50%, 75%, 90%, 95%, 96%, 97%, 98%, 99%, or 100% purified. The nucleic acids of the invention encode the peptides described herein. In certain embodiments, the nucleic acids encode a peptide having the sequence of SEQ ID NO: 1-146 or combinations thereof. Nucleic acids of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Nucleic acids of the invention can be isolated. An "isolated" nucleic acid is one that is not immediately contiguous with one or both of the 5' and 3' flanking genomic sequences that it is naturally associated with. An isolated nucleic acid can be, e.g., a recombinant DNA molecule of any length, provided that the nucleic acid sequence naturally found immediately flanking the recombinant DNA molecule in a naturally-occurring genome is removed or absent. Isolated nucleic acids can also include non-naturally occurring nucleic acid molecules. Nucleic acids of the invention can also comprise fragments that encode immunogenic peptides. Nucleic acids of the invention can encode full-length polypeptides, peptide fragments, and variant or fusion peptides.

Nucleic acids of the invention can be isolated, at least in part, from nucleic acid sequences present in, for example, a biological sample, such as blood, serum, saliva, or tissue from an infected individual. Nucleic acids can also be synthesized in the laboratory, for example, using an automatic synthesizer. An amplification method such as PCR can be used to amplify nucleic acids, at least in part, from either genomic DNA or cDNA encoding the polypeptides.

Nucleic acids of the invention can comprise coding sequences for naturally occurring polypeptides or can encode altered sequences that do not occur in nature. If desired, nucleic acids can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A nucleic acid of the invention is operably linked when it is positioned adjacent to or close to one or more expression control elements, which direct transcription and/or translation of the polynucleotide.

Thus, for example, a peptide of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably linked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al., Molecular Cloning, A Laboratory Manual, current edition, Cold Spring Harbor Laboratory, New York; Miller et al, Genetic Engineering, 8:277-298 (Plenum Press, current edition), Wu et al., Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al, Eds.,) John Wiley & Sons, NY (current edition), and references cited therein.

Accordingly, the invention also provides vectors comprising nucleic acids of the invention, and host cells comprising such vectors. In certain embodiments, the vector is a shuttle vector. In other embodiments, the vector is an expression vector (e.g., a bacterial or eukaryotic expression vector). In certain embodiments, the host cell is a bacterial cell. In other embodiments, the host cell is a eukaryotic cell.

Suitable host cells or cell lines for the recombinant nucleic acids or vectors of the invention transfection by this method include bacterial cells. For example, various strains of *E. coli* (e.g., HB101, MC1061) are well-known as host cells in the field of biotechnology. Various strains of *B. subtilis, Pseudomonas, Streptomyces*, and other bacilli and the like can also be employed in this method. Alternatively, a peptide of the invention can be expressed in yeast, insect, mammalian, or other cell types, using conventional procedures. Cell-free in vitro synthesis and/or enzyme-mediated synthetic machineries may also be used.

The present invention also provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g., a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like, affinity chromatography, such as with inorganic ligands or monoclonal antibodies, size exclusion chromatography, immobilized metal chelate chromatography, gel electrophoresis, and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g., SDS-PAGE), capillary electrophoresis, column chromatography (e.g., high performance liquid chromatography (HPLC)), amino-terminal amino acid analysis, and quantitative amino acid analysis.

Methods

In another aspect, the invention provides methods of detecting in a sample an antibody to an epitope of a *Borrelia* antigen. In certain embodiments, the methods comprise contacting a sample with a peptide of the invention, and detecting formation of an antibody-peptide complex comprising said peptide, wherein formation of said complex is indicative of the presence of an antibody to an epitope of a *Borrelia* antigen in said sample. In certain embodiments, the *Borrelia* antigen is from an infectious *Borrelia* species. In certain embodiments, the *Borrelia* antigen is from a pathogenic *Borrelia* species, such as *Borrelia burgdorferi sensu stricto, Borrelia afzelli*, or *Borrelia garinii*. Other species of *Borrelia* which have been implicated in Lyme disease, such as *B. lusitaniae* and *B. valaisianae*, can also be detected using the methods of the invention, provided they induce antibodies which can react specifically with a peptide of the invention. Thus, it is to be understood that the term "pathogenic *Borrelia*," as used herein, refers to any such *Borrelia* species that causes Lyme disease.

In certain embodiments, the methods comprise contacting the sample with a mixture of two, three, four, or more (e.g., 5, 6, 7, 8, 9, 10, 15, 20, 25, 30, 40, 50, 60, 70, 80, 90, 100, 150, 200, 250, 300, 400, 500, or more) different peptides of the invention. In certain embodiments, the methods comprise contacting the sample with a mixture of one or more peptides of the invention and one or more other peptides (e.g., a *Borrelia* peptide, or antigenic fragment or epitope thereof, such as an OspA, OspB, DbpA, flagella-associated proteins FlaA (p37) and FlaB (p41), OspC (25 kd), BBK32, BmpA (p39), p21, p39, p66, p83, or VlsE protein).

In certain embodiments, the peptide or each peptide in the mixture is an isolated (e.g., synthetic and/or purified) peptide. In certain embodiments, the peptide or mixture of peptides is attached to or immobilized upon a solid support. In certain embodiments, the solid support is a bead (e.g., a colloidal particle, nanoparticle, latex bead, etc.), a flow path in a lateral flow immunoassay device (e.g., a porous membrane), a flow path in an analytical rotor, a blot (Western blot, dot blot, or slot blot), a tube or a well (e.g., in a plate suitable for an ELISA assay), or a sensor (e.g., an electrochemical, optical, or opto-electronic sensor).

In certain embodiments, the detecting step comprises performing an ELISA assay. In other embodiments, the detecting step comprises performing a lateral flow immunoassay. In other embodiments, the detecting step comprises performing an agglutination assay. In other embodiments, the detecting step comprises spinning the sample in an analytical rotor. In still other embodiments, the detecting step comprises analyzing the sample with an electrochemical, optical, or opto-electronic sensor.

There are a number of different conventional assays for detecting formation of an antibody-peptide complex comprising a peptide of the invention. For example, the detecting step can comprise performing an ELISA assay, performing a lateral flow immunoassay, performing an agglutination assay, performing a Western blot, slot blot, or dot blot, analyzing the sample in an analytical rotor, or analyzing the sample with an electrochemical, optical, or opto-electronic sensor. These different assays are described above and/or are well-known to those skilled in the art.

In one embodiment, the methods involve detecting the presence of naturally occurring antibodies against a *Borrelia* antigen (e.g., the antigen of a pathogenic *Borrelia*, such as *B. Burgdorferi*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

Suitable immunoassay methods typically include: receiving or obtaining (e.g., from a patient) a sample of body fluid or tissue likely to contain antibodies; contacting (e.g., incubating or reacting) a sample to be assayed with a peptide of the invention, under conditions effective for the formation of a specific peptide-antibody complex (e.g., for specific binding of the peptide to the antibody); and assaying the contacted (reacted) sample for the presence of an antibody-peptide reaction (e.g., determining the amount of an antibody-peptide complex). The presence of an elevated amount of the antibody-peptide complex indicates that the subject was exposed to and infected with an infectious *Borrelia* species. A peptide, including a modified form thereof, which "binds specifically" to (e.g., "is specific for" or binds "preferentially" to) an antibody against a *Borrelia* antigen interacts with the antibody, or forms or undergoes a physical association with it, in an amount and for a sufficient time to allow detection of the antibody. By "specifically" or "preferentially," it is meant that the peptide has a higher affinity (e.g., a higher degree of selectivity) for such an antibody than for other antibodies in a sample. For example, the peptide can have an affinity for the antibody of at least about 1.5-fold, 2-fold, 2.5-fold, 3-fold, or higher than for other antibodies in the sample. Such affinity or degree of specificity can be determined by a variety of routine procedures, including, e.g., competitive binding studies. In an ELISA assay, a positive response is defined as a value 2 or 3 standard deviations greater than the mean value of a group of healthy controls. In some embodiments, a second tier assay is required to provide an unequivocal serodiagnosis of Lyme disease.

Phrases such as "sample containing an antibody" or "detecting an antibody in a sample" are not meant to exclude samples or determinations (e.g., detection attempts) where no antibody is contained or detected. In a general sense, this invention involves assays to determine whether an antibody produced in response to infection with an infectious *Borrelia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc).

The methods comprise receiving or obtaining a sample of body fluid or tissue likely to contain antibodies from a subject. The antibodies can be, e.g., of IgG, IgE, IgD, IgM, or IgA type. Generally, IgM and/or IgA antibodies are detected, e.g., for detection at early stages of infection. Although, in the case of a *Borrelia* infection, IgM antibodies can persist for a long time. IgG antibodies can be detected when some of the additional peptides discussed above are used in the method (e.g., peptides for the detection of flagellum proteins). The sample is preferably easy to obtain and may be serum or plasma derived from a venous blood sample or even from a finger prick. Tissue from other body parts or other bodily fluids, such as cerebro-spinal fluid (CSF), saliva, gastric secretions, mucus, urine, etc., are known to contain antibodies and may be used as a source of the sample.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

In certain embodiments of the invention, the assay comprises: immobilizing the antibody(s) in the sample, e.g., directly or indirectly via binding to peptides of the invention; adding a peptide of the invention; and detecting the degree of antibody bound to the peptide, e.g., by the peptide being labeled or by adding a labeled substance, such as a labeled binding partner (e.g., streptavidin-colloidal gold complex) or a labeled antibody which specifically recognizes the peptide. See, e.g., FIG. 1. In other embodiments, the assay comprises: immobilizing a peptide of the invention; adding the sample containing antibodies; and detecting the amount of antibody bound to the peptide, e.g., by adding another peptide of the invention conjugated, directly or indirectly, to a label (e.g., colloidal gold complex, fluorescent label, enzyme (e.g., horseradish peroxidase or alkaline phosphatase)) or by adding a labeled substance, such as a binding partner or a labeled antibody which specifically recognizes the sample antibodies (e.g., anti-human IgG antibodies, anti-human IgM antibodies, anti-dog IgG antibodies, anti-dog IgM antibodies, protein A, protein G, protein L, etc.) or combinations thereof. See, e.g., FIG. 3. In other embodiments, the assay comprises: immobilizing a peptide of the invention; adding the sample containing antibodies; and detecting the amount of antibody bound to the peptide, e.g., by adding a first binding partner which specifically recognizes the sample antibodies (e.g., anti-human IgG antibodies, anti-human IgM antibodies, anti-dog IgG antibodies, anti-dog IgM antibodies, protein A, protein G, protein L, etc.), and further adding a second binding partner (e.g., protein A, protein G, protein L, etc.), wherein the second binding partner is labeled and recognizes said first binding partner. In still other embodiments, the assay comprises: reacting the peptide and the sample containing antibodies without any of the reactants being immobilized, and then detecting the amount of complexes of antibody and peptide, e.g., by the peptide being labeled or by adding a labeled substance, such as a labeled binding partner (e.g., streptavidin-colloidal gold complex) or a labeled antibody which specifically recognizes the peptide.

Immobilization of a peptide of the invention can be either covalent or non-covalent, and the non-covalent immobilization can be non-specific (e.g., non-specific binding to a polystyrene surface in, e.g., a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin, neutravidin, or an analogue thereof. An alternative is a situation in which the moiety has the amino acid sequence His-His-His-His-His-His (SEQ ID NO: 152) and the carrier comprises a Nitrilotriacetic Acid (NTA) derivative charged with $Ni^{++}$ or $Co^{++}$ ions. In certain embodiments, the moiety is a fusion partner, e.g., BSA. In exemplary embodiments, peptides of the invention may be conjugated to BSA via N-terminal and/or C-terminal residues of the peptides. In one embodiment, one, two, three, four, five, 10, 15, 20, 25, 30 or more peptides of the invention may be substituted into, e.g., conjugated with BSA. As would be understood by one skilled in the art, substitution levels may impact the sensitivity of the assay. Lower concentrations of highly substituted BSA are needed to achieve sensitivity offered by high concentrations of BSA-peptide containing fewer molecules of peptide. In certain other embodiments, the fusion partner may be MAPS. In certain exemplary embodiments, MAPS may consist of 4, 8, or more asymmetric branches.

Suitable carriers, supports, and surfaces include, but are not limited to, beads (e.g., magnetic beads, colloidal particles or nanoparticles, such as colloidal gold, or nanoparticles comprising silica, latex, polystyrene, polycarbonate, or PDVF), latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In certain embodiments, a peptide of the invention is immobilized on a solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices (e.g., lateral flow immunoassay devices), dipsticks, and immunocapillary or immunochromatographic immunoassay devices.

In embodiments of the invention, the solid or semi-solid surface or carrier is the floor or wall in a microtiter well, a filter surface or membrane (e.g., a nitrocellulose membrane or a PVDF (polyvinylidene fluoride) membrane, such as an Immobilon™ membrane), a hollow fiber, a beaded chromatographic medium (e.g., an agarose or polyacrylamide gel), a magnetic bead, a fibrous cellulose matrix, an HPLC matrix, an FPLC matrix, a substance having molecules of such a size that the molecules with the peptide bound thereto, when dissolved or dispersed in a liquid phase, can be retained by means of a filter, a substance capable of forming micelles or participating in the formation of micelles allowing a liquid phase to be changed or exchanged without entraining the micelles, a water-soluble polymer, or any other suitable carrier, support or surface.

In some embodiments of the invention, the peptide is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACS), detection of a radioactively labeled agent by autoradiography, electron microscopy, immunostaining, subcellular fractionation, or the like. In one embodiment, a radioactive element (e.g., a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody or other binding agent (e.g., protein A, protein G, protein L) which binds to the first antibody. This secondary antibody or other binding agent can be labeled, e.g., with a radioactive, enzymatic, fluorescent, luminescent, or other detectable label, such as an avidin/biotin system. In another embodiment, the binding partner is a peptide of the invention, which can be conjugated directly or indirectly (e.g. via biotin/avidin interaction) to an enzyme, such as horseradish peroxidase or alkaline phosphatase or other signaling moiety. In the case of enzyme, the detectable signal is produced by adding a substrate of the enzyme that produces a detectable signal, such as a chromogenic, fluorogenic, or chemiluminescent substrate.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

A particularly useful assay format is a lateral flow immunoassay format. Antibodies to human or animal (e.g., dog, mouse, deer, etc.) immunoglobulins, or staph A or G protein antibodies, can be labeled with a signal generator or reporter (e.g., colloidal gold) that is dried and placed on a glass fiber pad (sample application pad or conjugate pad). The diagnostic peptide is immobilized on membrane, such as nitrocellulose or a PVDF (polyvinylidene fluoride) membrane (e.g., an Immobilon™ membrane). When a solution of sample (blood, serum, etc.) is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide are present, they bind to the diagnostic peptide striped on the membrane, thereby generating a signal (e.g., a band that can be seen or visualized). An additional antibody specific to the labeled antibody or a second labeled antibody can be used to produce a control signal.

Figure 2:
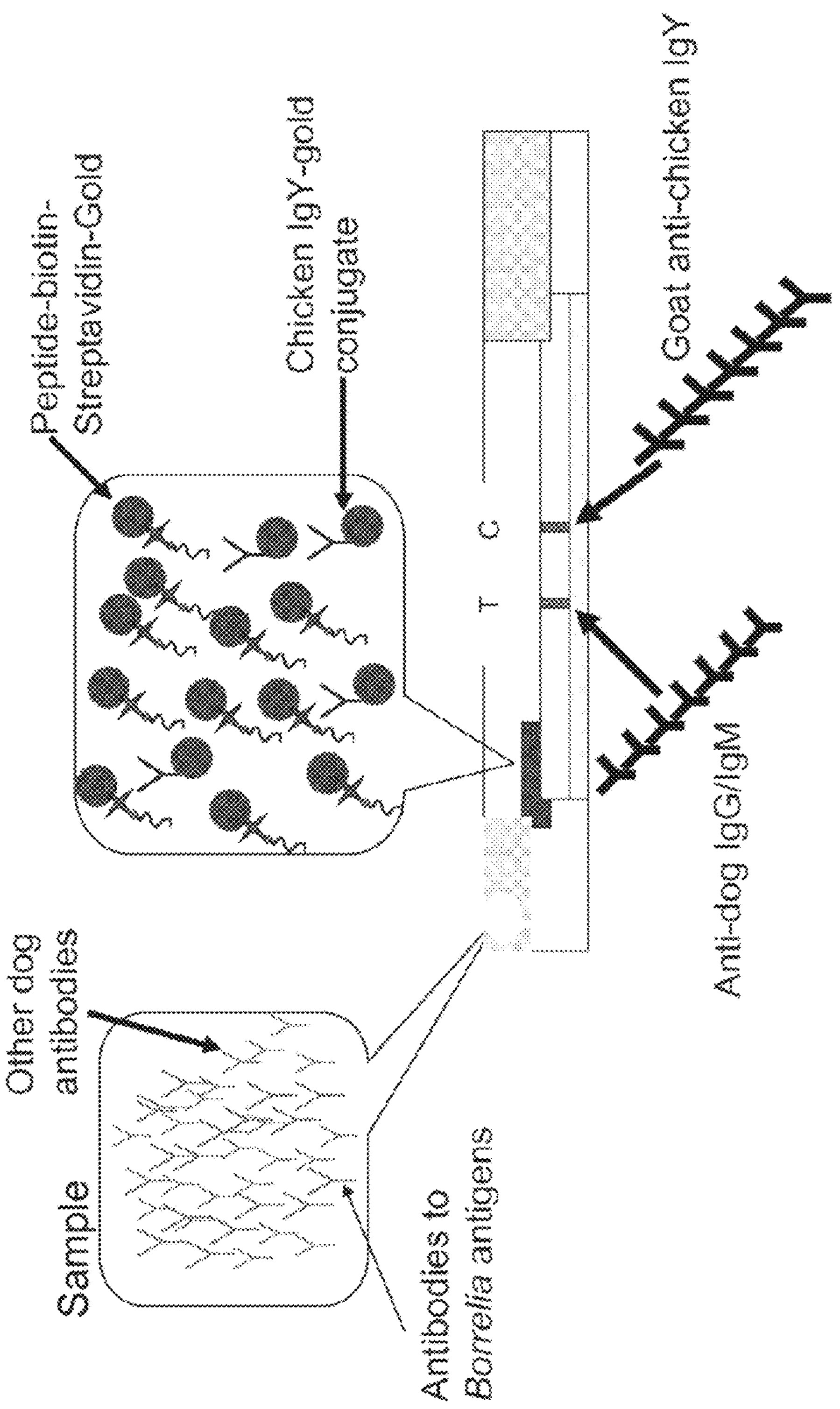
FIG. 2 is a diagram of a lateral flow immunoassay device based on the indirect sandwich assay of FIG. 1. In this embodiment of a lateral flow immunoassay device, sample is applied at a sample loading pad and then flows through the conjugate pad to the test membrane. Peptide-biotin-streptavidin-gold complexes are solubilized as the sample passes through the conjugate pad and complexes between peptides of the invention and appropriate anti-*Borrelia* antigen antibodies are then formed. The test site comprises sample appropriate anti-IgG or anti-IgM antibodies, which bind to all antibodies in the sample. Protein L, for example, can be used in place of anti-IgG or anti-IgM antibodies. If sufficient antibodies in the sample have bound to peptides of the invention, a positive signal will appear at the test site. In another embodiment of a lateral flow immunoassay device, peptides of the invention are immobilized at the test site (T) and sample appropriate anti-IgG or anti-IgM antibodies (e.g. anti-human or anti-canine) conjugated to a detectable label (e.g. colloidal gold particles) are present in the conjugate pad. Sample passing through the conjugate pad solubilizes the labeled antibodies and any anti-*Borrelia* antigen antibodies present in the test sample bind to the labeled antibodies and such antibody complexes are captured by the immobilized *Borrelia* peptides of the invention at the test site, thereby producing a positive signal. In either embodiment, the device can further comprise a control site (C) at which binding partners that recognize the labeled peptide or labeled antibody in the conjugate pad is immobilized.
Figure 3:
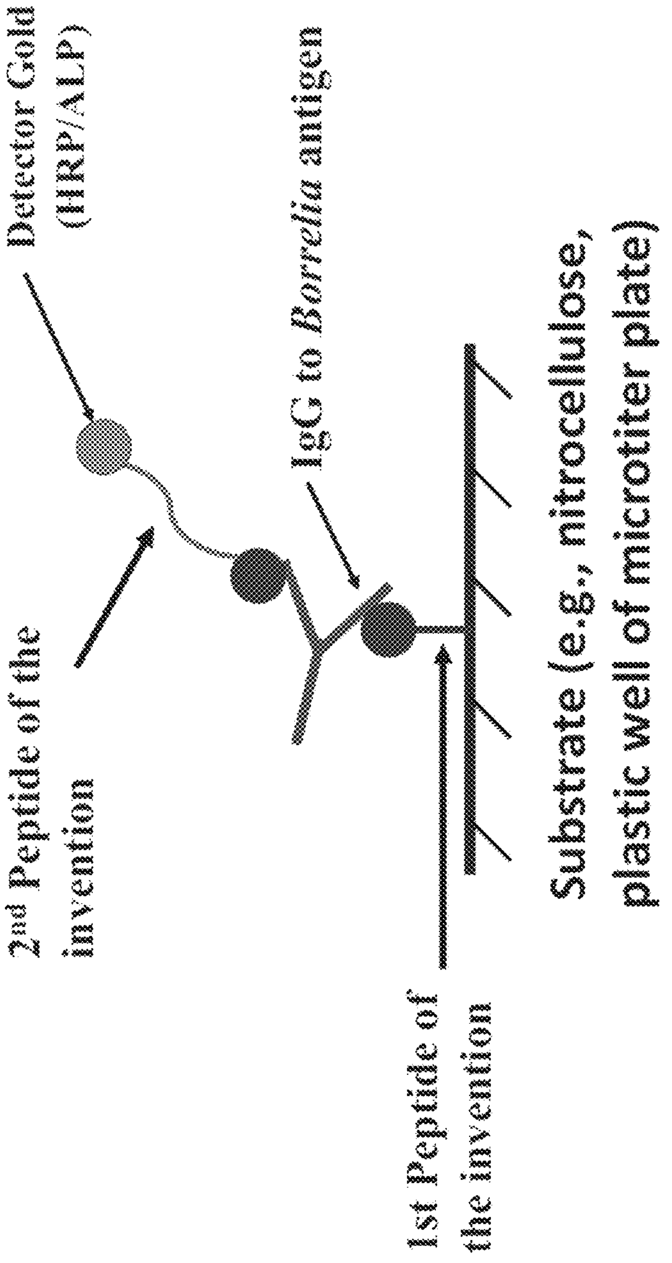
FIG. 3 is a diagram of a double antigen sandwich assay which can be used to detect antibodies to *Borrelia* antigens. In this embodiment, peptides of the invention are immobilized to a suitable substrate (e.g., nitrocellulose membrane, well of an ELISA plate) at a test site. Antibodies in a test sample are bound by the immobilized peptides of the invention. Test sample antibodies to appropriate *Borrelia* antigens will then bind to a second set of peptides of the invention that are conjugated to a detector molecule (e.g., colloidal gold, horse radish peroxidase (HRP), alkaline phosphatase (ALP)), which detects the presence of the antibodies bound to the first set of peptides immobilized at the test site.
Figure 4:
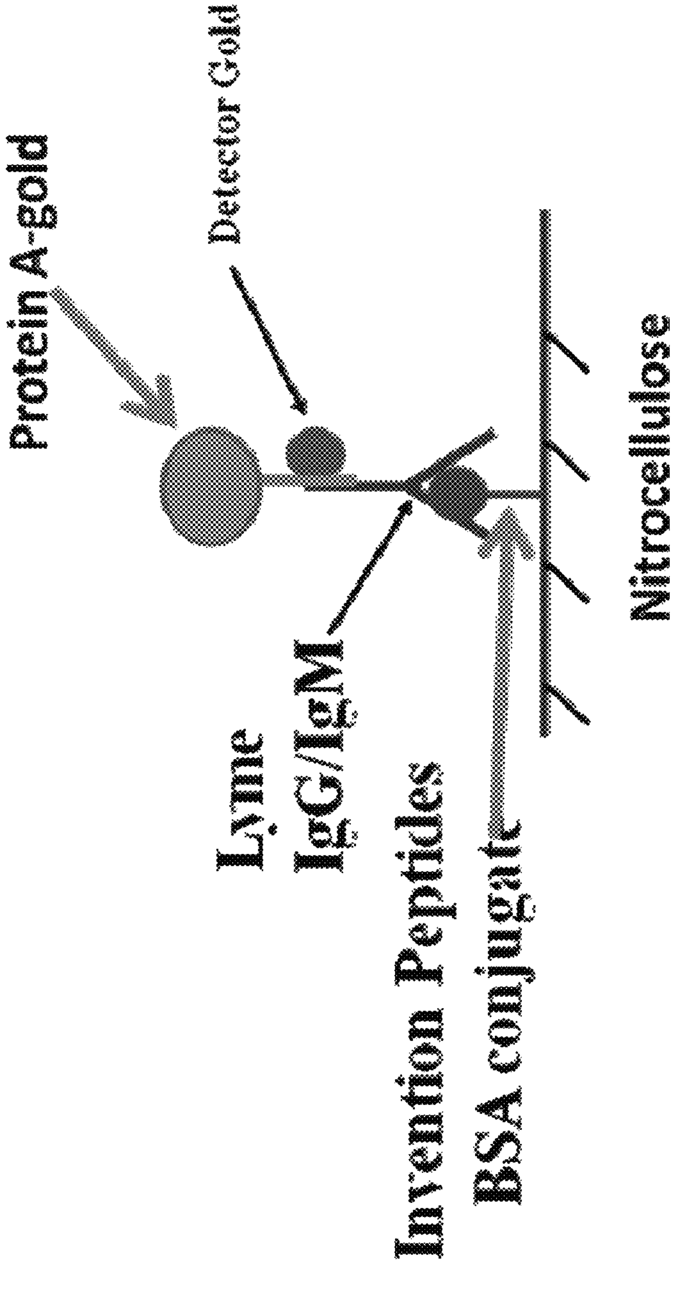
FIG. 4 is a diagram of a lateral flow immunoassay device which can be used to detect antibodies to *Borrelia* antigens. In this embodiment of a lateral flow immunoassay device, peptides of the invention are immobilized to a suitable substrate (e.g., nitrocellulose membrane) at a test site. Anti-*Borrelia* antibodies in a test sample are bound by the immobilized peptides of the invention. Gold-conjugated protein A and/or gold-conjugated protein G is added to the system and binds to the Fc portion of the captured anti-*Borrelia* antibody, thereby producing a positive signal. In this embodiment, the device can further comprise a control site at which binding partners that recognize the gold-conjugated protein A and/or gold-conjugated protein G are immobilized. Such binding partners may include, but are not limited to, anti-protein A, anti-protein G, mouse IgG, and/or other similar IgG molecules.
Figure 5:
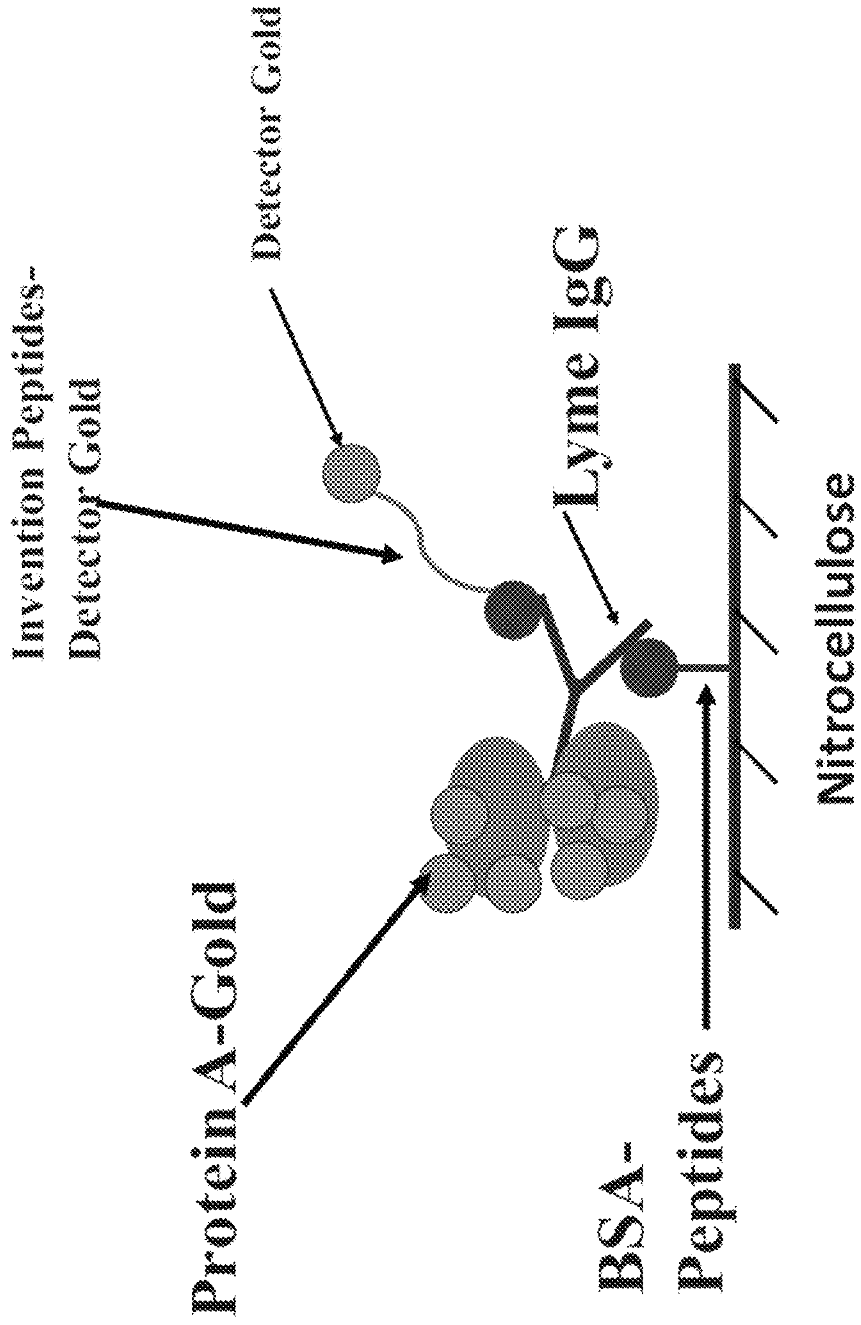
FIG. 5 is a diagram of a lateral flow immunoassay device which can be used to detect antibodies to *Borrelia* antigens. In this embodiment of a lateral flow immunoassay device, peptides of the invention are immobilized to a suitable substrate (e.g., nitrocellulose membrane) at a test site. Anti-*Borrelia* antibodies in a test sample are bound by the immobilized peptides of the invention. Anti-*Borrelia* antibodies can be detected by gold-conjugated peptides of the invention, thereby producing a positive signal. Gold-conjugated protein A and/or gold-conjugated protein G can be added to the system to enhance the signal by binding to the Fc portion of the captured anti-*Borrelia* antibody. In this embodiment, the device can further comprise a control site at which binding partners that recognize the gold-conjugated protein A and/or gold-conjugated protein G are immobilized. Such binding partners may include, but are not limited to, anti-protein A, anti-protein G, mouse IgG, and/or other similar IgG molecules.

An alternative format for the lateral flow immunoassay comprises the peptides or compositions of the invention being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM or anti-animal (e.g., dog, mouse, deer) IgG/IgM antibodies or other peptides of the invention are immobilized on a membrane, such as nitrocellulose of PVDF, at a test site (e.g., a test line). When sample is added to the sample application pad, antibodies in the sample react with the labeled peptide complexes such that antibodies that bind to peptides of the invention become indirectly labeled. The antibodies in the sample are then transported into the next membrane (PVDF or nitrocellulose containing the diagnostic peptide) by capillary action and bind to the immobilized anti-human IgG/IgM or anti-animal IgG/IgM antibodies (or protein A, protein G, protein L, or combinations thereof) or immobilized peptides of the invention. If any of the sample antibodies are bound to the labeled peptides of the invention, the label associated with the peptides can be seen or visualized at the test site. One embodiment of this type of lateral flow device is shown in FIG. 2. Another embodiment of this type of lateral flow device in which the peptides of the invention are used both as the immobilized capture agent at a test site and as a soluble labeled complex to react with antibodies in a sample is shown in FIG. 3. Suitable controls for this assay can include, e.g., a chicken IgY-colloidal gold conjugate located at the sample application pad or conjugate pad, and an anti-chicken IgY antibody immobilized at a control site located proximal to the test site.

In the embodiments utilizing the lateral flow immunoassay format described above, the lateral flow device may comprise two ports: a sample port, which is positioned between a conjugate pad (containing a labeled analyte-binding partner) and a test site or line (containing an immobilized analyte-binding partner) and a chase port, which is positioned upstream (e.g. toward the end of the device away from test site) of the conjugate pad. In such devices comprising two ports, sample is deposited upstream of the test site via the sample port and fluid flow through the conjugate pad is initiated by depositing solution (e.g. diluent, buffer, or the like) via the chase port. The "chase" solution dissolves the labeled reagents in the conjugate pad and flows through to interact with the same and immobilized reagents at the test site.

Another assay for the screening of blood products or other physiological or biological fluids is an enzyme linked immunosorbent assay, i.e., an ELISA. Typically in an ELISA, isolated peptides or compositions of the invention are adsorbed to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-*Borrelia* (e.g., *B. burgdorferi*) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin (αHuIg) from another animal, such as dog, mouse, cow, etc.) or another peptide of the invention that is conjugated to an enzyme or other label by standard procedures and is dissolved in blocking buffer. The label can be chosen from a variety of enzymes, including horseradish peroxidase (HRP), beta-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where Lyme disease is not endemic, or by other such conventional definitions. In the case of a very specific assay, OD+2 SD can be used as a cutoff value.

In one embodiment of an ELISA, a peptide or a mixture of peptides of the invention is immobilized on a surface, such as a ninety-six-well ELISA plate or equivalent solid phase that is coated with streptavidin or an equivalent biotin-binding compound, such as avidin or nuetravidin, at an optimal concentration in an alkaline coating buffer and incubated at 4° C. overnight. After a suitable number of washes with standard washing buffers, an optimal concentration of a biotinylated form of a peptide or composition of the invention, dissolved in a conventional blocking buffer, is applied to each well. A sample is then added, and the assay proceeds as above. Conditions for performing ELISA assays are well-known in the art.

In another embodiment of an ELISA, a peptide or a mixture of peptides of the invention is immobilized on a surface, such as a ninety-six-well ELISA plate or equivalent solid phase via a fusion partner, e.g., BSA or MAPS. A sample is then added and the assay proceeds as above.

In another embodiment, the methods comprise an agglutination assay. For example, in certain embodiments, colloidal particles (e.g., colloidal gold, etc.) or latex beads are conjugated to peptides or compositions of the invention. Subsequently, the biological fluid is incubated with the bead/peptide conjugate, thereby forming a reaction mixture. The reaction mixture is then analyzed to determine the presence of the antibodies. In certain embodiments, the agglutination assays comprise the use of a second population of particles, such as colloidal particles (e.g., colloidal gold, etc.) or latex beads, conjugated to (1) antibodies specific to the peptides of compositions of the invention, in the case of a competition assay, or (2) antibodies capable of detecting sample antibodies (e.g., anti-human IgG or IgM antibodies, anti-dog IgG or IgM antibodies, etc.), in the case of a sandwich assay. Suitable agglutination methods can comprise centrifugation as a means of assessing the extent of agglutination.

In still other embodiment, peptide or compositions of the invention are electro- or dot-blotted onto nitrocellulose paper. Subsequently, a sample, such as a biological fluid (e.g., serum or plasma) is incubated with the blotted antigen, and antibody in the biological fluid is allowed to bind to the antigen(s). The bound antibody can then be detected, e.g., by standard immunoenzymatic methods or by visualization using colloidal nanoparticles couples to secondary antibodies or other antibody binding agents, such as protein A, protein G, protein L, or combinations thereof.

It should be understood by one of skill in the art that any number of conventional protein assay formats, particularly immunoassay formats, may be designed to utilize the isolated peptides of this invention for the detection of *Borrelia* antibodies and infection by pathogenic *Borrelia* (e.g., *B. burgdorferi*) in a subject. This invention is thus not limited by the selection of the particular assay format, and is believed to encompass assay formats that are known to those of skill in the art.

In certain embodiments, the sample used in the methods is a bodily fluid, such as blood, serum, cerebral spinal fluid, urine, or saliva. In other embodiments, the sample is a tissue (e.g., a tissue homogenate) or a cell lysate. In certain embodiments, the sample is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human.

Much of the preceding discussion is directed to the detection of antibodies against pathogenic *Borrelia*. However, it is to be understood that the discussion also applies to the detection of primed T-cells, either in vitro or in vivo.

It is expected that a cell-mediated immune response (e.g., a T-helper response) is generated, since IgG is produced. It is therefore expected that it will be possible to determine the immunological reactivity between primed T-cells and a peptide of the invention. In vitro this can be done by incubating T-cells isolated from the subject with a peptide of the invention and measuring the immunoreactivity, e.g., by measuring subsequent T-cell proliferation or by measuring release of cytokines from the T-cells, such as IFN-γ. These methods are well-known in the art.

When a method of the invention is carried out in vivo, any of a variety of conventional assays can be used. For example, one can perform an assay in the form of a skin test, e.g., by intradermally injecting, in the subject, a peptide of the invention. A positive skin reaction at the location of injection indicates that the subject has been exposed to and infected with a pathogenic *Borrelia* capable of causing Lyme disease, and a negative skin response at the location of injection indicates that the subject has not been so exposed/infected. This or other in vivo tests rely on the detection of a T-cell response in the subject.

In another aspect, the invention provides methods of diagnosing Lyme disease in a subject. The subject can be a subject suspected of having antibody against a causative agent of Lyme disease. The diagnostic method is useful for diagnosing subjects exhibiting the clinical symptoms of Lyme disease.

In certain embodiments, the methods comprise contacting a sample from the subject with a peptide of the invention, and detecting formation of an antibody-peptide complex comprising said peptide, wherein formation of said complex is indicative of the subject having Lyme disease. In certain embodiments, the methods comprise contacting the sample with a mixture of two, three, four, or more (e.g., 5, 6, 7, 8, 9, 10, 15, 20, 25, 30, 40, 50, 60, 70, 80, 90, 100, 150, 200, 250, 300, 400, 500, or more) different peptides of the invention. In certain embodiments, the methods comprise contacting the sample with a mixture of one or more peptides or the invention and one or more other peptides (e.g., a *Borrelia* peptide, or antigenic fragment or epitope thereof, such as an OspA, OspB, DbpA, flagella-associated proteins FlaA (p37) and FlaB (p41), OspC (25 kd), BBK32, BmpA (p39), p21, p39, p66, p83, or VlsE protein).

In certain embodiments, the peptide or each peptide in the mixture is an isolated (e.g., synthetic and/or purified) peptide. In certain embodiments, the peptide or mixture of different peptides is attached to or immobilized upon a substrate (e.g., a solid or semi-solid support). For example, in certain embodiments, the substrate is a bead (e.g., a colloidal or other type of particle or nanoparticle), a flow path in a lateral flow immunoassay device (e.g., a porous membrane), a blot (e.g., a Western blot, dot blot, or slot blot), a flow path in an analytical rotor, or a tube or a well (e.g., in a plate suitable for an ELISA assay).

There are a number of different conventional assays for detecting formation of an antibody-peptide complex comprising a peptide of the invention. For example, the detecting step can comprise performing an ELISA assay, performing a lateral flow immunoassay, performing an agglutination assay, analyzing the sample using a Western blot, a slot blot, or a dot blot, analyzing the sample in an analytical rotor, or analyzing the sample with an electrochemical, optical, or opto-electronic sensor. These different assays are described above and/or are well-known to those skilled in the art.

In certain embodiments, the sample is a bodily fluid, such as blood, serum, cerebral spinal fluid, urine, or saliva. In other embodiments, the sample is a tissue (e.g., a tissue homogenate) or a cell lysate. In certain embodiments, the subject is a wild animal (e.g., a deer or rodent, such as a mouse, chipmunk, squirrel, etc.). In other embodiments, the subject is a lab animal (e.g., a mouse, rat, guinea pig, rabbit, monkey, primate, etc.). In other embodiments, the subject is a domesticated or feral animal (e.g., a dog, a cat, a horse). In still other embodiments, the subject is a human.

Kits

In yet another aspect, the invention provides kits. In certain embodiments, the kits comprise a peptide of the invention. In certain embodiments, the kits comprise two, three, four, or more different peptides of the invention. The peptides can comprise a sequence of SEQ ID NO: 1 or SEQ ID NO: 2. In certain embodiments, the peptides are attached to or immobilized on a solid support. For example, in certain embodiments, the solid support is a bead (e.g., a colloidal particle or a nanoparticle), a flow path in a lateral flow immunoassay device, a flow path in an analytical rotor, or a tube or a well (e.g., in a plate).

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical rotor, a Western blot, a dot blot, a slot blot, or an electrochemical, optical, or opto-electronic sensor. The population of beads, the plate, and the devices are useful for performing an immunoassay. For example, they can be useful for detecting formation of an antibody-peptide complex comprising an antibody from a sample and a peptide of the invention. In certain embodiments, a peptide, a mixture of different peptides of the invention, or a peptide composition of the invention is attached to or immobilized on the beads, the plate, or the device.

In addition, the kits can include various diluents and buffers, labeled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, monoclonal antibody detector antibodies, an anti-mouse, anti-dog, anti-chicken, or anti-human antibody with indicator molecule conjugated thereto, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

Such kits provide a convenient, efficient way for a clinical laboratory to diagnose infection by a pathogenic *Borrelia*, such as a *B. burgdorferi*. Thus, in certain embodiments, the kits further comprise an instruction. For example, in certain embodiments, the kits comprise an instruction indicating how to use a peptide of the invention to detect an antibody to a *Borrelia* antigen or to diagnose Lyme disease. In certain embodiments, the kits comprise an instruction indicating how to use a population of beads, a plate, or a device (e.g., comprising a peptide or a mixture of different peptides of the invention) to detect an antibody to a *Borrelia* antigen or to diagnose Lyme disease.

The peptides, compositions and devices comprising the peptides, kits and methods of the invention offer a number of advantages. For example, they allow for simple, inexpensive, rapid, sensitive and accurate detection of Lyme disease, and avoid serologic cross-reactivity with other conditions with “Lyme-like” symptoms, such as myalgias, arthralgias, malaise or fever, including conditions such as syphilis, chronic arthritis, and multiple sclerosis. This allows for an accurate diagnosis. Furthermore, a diagnostic test of the invention (e.g., an ELISA assay, lateral flow immunoassay, or agglutination assay) is useful in serum samples that contain anti-OspA antibodies or other antibodies produced in response to a vaccine based on the outer surface proteins of *Borrelia*. A VlsE IR6 peptide of the invention does not cross-react with such antibodies, thereby allowing the differentiation of vaccinated individuals from individuals who were naturally infected with *B. burgdorferi.*

To the extent that any definitions in documents incorporated by reference are inconsistent with the definitions provided herein, the definitions provided herein are controlling. Although the invention has been described with reference to the presently preferred embodiments, it should be understood that various changes and modifications, as would be obvious to one skilled in the art, can be made without departing from the spirit of the invention. Accordingly, the invention is limited only by the following claims.

The disclosures, including the claims, figures and/or drawings, of each and every patent, patent application, and publication cited herein are hereby incorporated herein by reference in their entireties.

What is claimed:

1. A method for detecting in a sample an antibody to an epitope of a *Borrelia* antigen, the method comprising:

contacting a sample with a mixture of isolated peptides comprising three or more different isolated peptides, wherein each isolated peptide comprises a sequence of L-K-K-D-D-N-I-A-A-A-X11-V-L-R-G-X16-X17-K-D-G-X21-F-A-X24-X25 (SEQ ID NO: 1) wherein X11 is an amino acid selected from the group consisting of V and L, X16 is an amino acid selected from the group consisting of L and I, X17 is an amino acid selected from the group consisting of A and V, X21 is an amino acid selected from the group consisting of R, D and N, X24 is an amino acid selected from the group consisting of I, W, and Y, and X25 is an amino acid selected from the group consisting of K and R; and detecting formation of an antibody-peptide complex comprising at least one of said isolated peptides, wherein formation of said complex is indicative of an antibody to an epitope of a *Borrelia* antigen being present in said sample.

2. The method of claim 1, wherein said *Borrelia* antigen is from a *Borrelia burgdorferi, Borrelia afzelli*, or *Borrelia garinii* species.

3. The method of claim 1, wherein at least one of said isolated peptides is immobilized to a solid support.

4. The method of claim 3, wherein said solid support is a bead, a flow path in a lateral flow assay device, a well in a microtiter plate, or a flow path in a rotor.

5. The method of claim 1, wherein said detecting step comprises:

(i) performing an ELISA assay, (ii) running a lateral flow assay, (iii) performing an agglutination assay, (iv) performing a Western blot, a slot blot, or dot blot, or (v) running the sample through an analytical rotor.

6. The method of claim 1, wherein said sample is from a human, canine, or equine subject.

7. The method of claim 1, wherein said sample is a blood, serum, cerebral spinal fluid, urine, or saliva sample.

8. A kit comprising a mixture of isolated peptides comprising three or more different isolated peptides, wherein each isolated peptide comprises a sequence of L-K-K-D-D-N-I-A-A-A-X11-V-L-R-G-X16-X17-K-D-G-X21-F-A-X24-X25 (SEQ ID NO: 1) wherein X11 is an amino acid selected from the group consisting of V and L, X16 is an amino acid selected from the group consisting of L and I, X17 is an amino acid selected from the group consisting of A and V, X21 is an amino acid selected from the group consisting of R, D and N, X24 is an amino acid selected from the group consisting of I, W, and Y, and X25 is an amino acid selected from the group consisting of K and R and a labeling reagent capable of binding to an antibody that recognizes an epitope of at least one of said isolated peptides.

9. The kit of claim 8, wherein at least one of said isolated peptides is attached to a solid support.

10. The kit of claim 8, wherein at least one of said isolated peptides is attached to a bead, a tube or a well, a lateral flow assay device, or an analytical rotor.

11. The kit of claim 8, wherein the labeling reagent is an anti-human or anti-canine IgG antibody conjugated to a detectable label.

12. The kit of claim 11, wherein the detectable label is colloidal gold particles.

* * * * *